(12) United States Patent
Crescenzi et al.

(10) Patent No.: US 8,512,752 B2
(45) Date of Patent: Aug. 20, 2013

(54) HYALURONIC ACID DERIVATIVES OBTAINED VIA "CLICK CHEMISTRY" CROSSLINKING

(75) Inventors: Vittorio Crescenzi, Abano Terme (IT); Ada Mascolo, legal representative, Rome (IT); Fabiana Crescenzi, legal representative, Rome (IT); Alberta Crescenzi, legal representative, Pomezia (IT); Flavia Crescenzi, legal representative, Rome (IT); Fulvia Crescenzi, legal representative, Preci (IT); Laura Crescenzi, legal representative, Rome (IT); Vittoria Crescenzi, legal representative, Rome (IT); Di Meo Chiara, Abano Terme (IT); Devis Galesso, Abano Terme (IT)

(73) Assignee: Fidia Farmaceutici S.p.A., Abano Terme (IT)

( * ) Notice: Subject to any disclaimer, the term of this patent is extended or adjusted under 35 U.S.C. 154(b) by 261 days.

(21) Appl. No.: 12/440,721

(22) PCT Filed: Sep. 5, 2007
(Under 37 CFR 1.47)

(86) PCT No.: PCT/EP2007/007758
§ 371 (c)(1),
(2), (4) Date: May 18, 2010

(87) PCT Pub. No.: WO2008/031525
PCT Pub. Date: Mar. 20, 2008

(65) Prior Publication Data
US 2010/0291171 A1    Nov. 18, 2010

(30) Foreign Application Priority Data

Sep. 11, 2006  (IT) .............................. MI2006A1726

(51) Int. Cl.
*A61K 31/728* (2006.01)
*A61K 31/738* (2006.01)
*A01N 43/04* (2006.01)

(52) U.S. Cl.
USPC ........... 424/488; 424/422; 424/279.1; 514/54

(58) Field of Classification Search
None
See application file for complete search history.

(56) References Cited

U.S. PATENT DOCUMENTS

| 4,582,865 A | 4/1986 | Balazs et al. |
| 5,017,229 A | 5/1991 | Burns et al. |
| 5,356,883 A | 10/1994 | Kuo et al. |
| 5,676,964 A | 10/1997 | Della Valle et al. |

FOREIGN PATENT DOCUMENTS

| WO | WO-2007/003054 | 1/2007 |
| WO | WO-2007/035296 | 3/2007 |
| WO | WO 2007035296 A2 * | 3/2007 |

OTHER PUBLICATIONS

Crescenzi, Vittorio et al., "Novel hydrogels via click chemistry: synthesis and potential biomedical application." Biomacromolecules, Jun. 2007, vol. 8, No. 6, pp. 1844-1850.

Luo, Y. et al., "Cross-linked hyaluronic acid hydrogel films: new biomaterials for drug delivery," J. Control Release, Oct. 3, 2000, vol. 69, No. 3, pp. 169-184.

Ossipov D.A. et al., "Poly(vinyl alcohol)-based hydrogels formed by "click chemistry"," Macromolecules, 2006, vol. 39, No. 5, pp. 1709-1718.

* cited by examiner

*Primary Examiner* — Robert A Wax
*Assistant Examiner* — H. Sarah Park
(74) *Attorney, Agent, or Firm* — Birch, Stewart, Kolasch & Birch, LLP

(57) ABSTRACT

Crosslinked derivatives of polycarboxylated polysaccharides are described, wherein at least one of the polysaccharide chains consists of hyaluronic acid or a derivative thereof, crosslinked by means of reactions of the "click chemistry" type and their use in the field of viscosupplementation, plastic surgery, oncologic and reconstructive surgery and also as matrices for controlled release systems of biologically and/or pharmacologically active molecules and/or macromolecules.

24 Claims, 24 Drawing Sheets 1,2,3 - Triazole Formation Via Huisgen 1,3 - Dipolar Cycloaddition "Click" Reaction scheme between an azide and an alkyne General structure of the crosslinked products described in the invention General structure of the polysaccharide blocks a) and b) which can be used in the cycloaddition reaction Hydrogel obtained the crosslinking of hyaluronic acid chains by means of Huisgen cycloaddition (azide-alkyne).

HYALURONIC ACID DERIVATIVES OBTAINED VIA "CLICK CHEMISTRY" CROSSLINKING

This Application is the National Phase Under 35 U.S.C. §371 of PCT International Application No. PCT/EP2007/007758 which has an International filing date of Sep. 5, 2007, which claims priority to Italian Application No. MI2006A001726 filed on Sep. 11, 2006. The entire contents of all applications listed above are hereby incorporated by reference.

The present invention relates to hyaluronic acid derivatives obtained via "Click Chemistry" crosslinking.

In particular, the present invention relates to crosslinked derivatives of hyaluronic acid and other polycarboxylated polysaccharides, crosslinked by means of one or more reactions of the "click chemistry" type, in particular 1,3-dipolar cycloadditions between alkyne and azide derivatives, the biocompatible hydrogels obtained from the above derivatives, having physico-chemical and rheological characteristics which can be modulated through the crosslinking degree, the process for the preparation of the above hydrogels by the formation of covalent bonds between two suitable derivatized polysaccharide blocks, and their use in the field of viscosupplementation, plastic surgery, and also in the medical field as cellular supports and/or matrices for controlled release systems of biologically or pharmacologically active molecules and/or macromolecules and for medicated gels in oncologic reconstructive surgery. It also relates to a process wherein these bioactive, i.e. biologically or pharmacologically active, molecules and/or macromolecules are physically incorporated inside the hydrogels directly during the above crosslinking of the polysaccharides and the consequent formation of the hydrogels themselves.

FIELD OF THE INVENTION

Hyaluronic acid (HA) is a natural linear heteropolysaccharide consisting of D-glucuronic acid and N-acetyl-glucosamine, with a molecular weight which can vary from 50,000 to 13,000,000 Da depending on its origin, practically present in every compartment of our organism. There are numerous roles physiologically exerted by HA: the mechanical supporting of the cells of many tissues, for example, lubrication of joints, modulation of numerous biological and physiological processes (among which proliferation, migration and cell differentiation, mediated by interaction with its membrane receptor CD44). The protection effect is also well-known of HA with respect to the degeneration of the cartilages of a joint damaged by a pathology or a trauma: in this situation proinflammatory cytokines, in particular Interleukine-1 (IL-1), are present in a strong concentration in the joint cavity. They promote the disintegration of the cartilage itself and inhibit chondrocyte proliferation (van Beuningen H. M. et al., *Arthritis Rheum,* 1991, 34:606-615). Various scientific experimentations show that hyaluronic acid is capable of contrasting the action of IL-1, drastically reducing its negative effects and exerting a reparatory effect on the cartilage tissue of the joint into which it is injected (Stove J. et al., *J Orthop Res,* 2002, 20:551-555). On a joint level, moreover, the hyaluronic acid contained in the synovial fluid acts as a viscous lubricant during slow movements, whereas as a result of its elastic properties it absorbs possible traumas or microtraumas which can affect the joint during rapid movements.

The tissue-hydrating and cicatrizant functions of HA are also widely known and exploited in the preparation of medications long used in the treatment of wounds, ulcers and various kinds of skin lesions (for example, Balasz A. et al., *Cosmetics & Toiletries,* 1984, 5:8-17).

The hyaluronic acid used in the present invention can derive from any source; it can be obtained for example by extraction from chicken combs (EP 138572 B1), or by fermentation (EP 716688 B1), and can have a molecular weight ranging from 50,000 to 3,000,000 Da.

The term "hyaluronic acid", as used in the scope of the present patent application, refers to both polysaccharide in its form of polycarboxylic acid and its salts, such as sodium, potassium, magnesium and calcium salt.

Numerous chemical modifications to which the HA molecule can be subjected are also known in the art, and are substantially:

salification with organic and/or inorganic bases (EP 138572 B1);

esterification of HA with alcohols of the aliphatic, araliphatic, cyclo-aliphatic, aromatic, cyclic and heterocyclic (HYAFF®) series, with an esterification percentage which can vary according to the type of alcohol used (EP 216453 B1);

amidation of HA with amines of the aliphatic, araliphatic, cyclo-aliphatic, aromatic, cyclic and heterocyclic (HYADD®) series, with an amidation percentage ranging from 0.1 to 50% (EP 1095064 B1);

O-sulphation of HA up to the $4^{th}$ sulphation degree (EP 702699 B1);

deacetylation of HA: the N-acetyl-glucosamine fraction is deacetylated in a deacetylation percentage preferably ranging from 0.1 to 30% (EP 1313772 B1);

percarboxylation of HA obtained from the oxidation of the primary hydroxyl of the N-acetyl-glucosamine fraction with a percarboxylation degree ranging from 0.1 to 100% (HYOXX®; patent application EP 1339753).

Although maintaining the biocompatibility, manageability and facility of use of the starting polysaccharide, the polymers obtained through these processes can have a different degradation rate in a physiological environment, a different hydrosolubility, a different mechanical profile, depending on the chemical modification applied to it.

A further chemical modification of HA consists in the crosslinking of polysaccharide chains via internal esterification (EP 341745 B1) to form a network (ACP®) with a higher molecular weight, whose density depends on the crosslinking degree reached; this process is useful for obtaining a biomaterial characterized by a lower biodegradation rate, and with higher viscoelasticity and mucoadhesion properties with respect to the starting substrate.

In order to obtain similar polymeric characteristics, a similar approach is represented by the chemical crosslinking of polysaccharide by the introduction of bifunctional linkers, as in the case of epoxides (De Belder et al., WO 86/00912), divinylsulfones in alkaline solution (E. A. Balazs et al., U.S. Pat. No. 4,582,865), biscarbodiimides (J. W. Kuo et al., U.S. Pat. No. 6,537,979) and various other reagents such as formaldehyde, dimethylurea, ethylene oxide, polyisocyanates (E. A. Balazs et al., UK 8420560).

Other specific examples of the preparation of hydrogels by the crosslinking of chemical derivatives of hyaluronic acid are described by D. Renier et al. (WO 02/18450), where partially N-deacetylated HA is used and the crosslinking is obtained by means of a multicomponent reaction, and D. Bellini et al. US 2005/0119219A1), where the covalent bond between the polysaccharide chains and the consequent formation of a gel are obtained following photochemical treatment of photo-reactive ester derivatives.

In most of the above documents of the state of the art, the use is described of gels obtained as dermal fillers in plastic surgery, as fluids for viscosupplementation in the treatment of intra-articular pathologies, as substitutive materials of vitreous humour in ophthalmic surgery, as mucoadhesive materials in the prevention of post-operative adherences, as biomaterials for the preparation of scaffolds in tissue engineering and/or as matrices for bioactive molecule release systems.

An objective of the present invention is consequently also to identify an alternative process to those described and used in the state of the art for the preparation of crosslinked derivatives of hyaluronic acid, an alternative process which has significant advantages.

An object of the present invention therefore relates to a process for the preparation of crosslinked derivatives of polycarboxylated polysaccharides, wherein at least one of the polysaccharide chains consists of hyaluronic acid or a derivative thereof, crosslinked by means of "click chemistry"-type reactions, said process comprising the following phases:

i) synthesis of partial derivatives (esters, amides, thioesters, anhydrides) of hyaluronic acid, and optionally another polycarboxylated polysaccharide or the respective salts or derivatives;

ii) cycloaddition reaction between the derivative obtained in phase i) with the formation of covalent bonds between the chains.

A further object of the present invention relates to the same crosslinked derivatives of polycarboxylated polysaccharides obtained in the above process, wherein at least one of the polysaccharide chains consists of hyaluronic acid or a derivative thereof, crosslinked by means of reactions of the "click chemistry" type.

The term "click chemistry" comprises and identifies various groups of chemical reactions characterized by particular properties such as rapidity, regioselectivity and high yield and having a high thermodynamic driving force, generally greater than or equal to 20 kcal/mol.

Among "click" reactions, cycloaddition reactions such as Diels-Alder reactions, and above all Huisgen 1,3-dipolar cycloadditions, are particularly significant in the present invention. An example of a cycloaddition consists of a reaction in which two unsaturated molecules react to form a cyclic compound with the formation of two new σ bonds using π electrons.

Diels-Alder reactions (O. Diels, K. Alder, *Ann.* 1928, 460, 98; O. Diels, K. Alder, *Ann.* 1929, 470, 62; O. Diels, K. Alder, *Ber.* 1929, 62, 2081 2087) are cyclo-additions [4+2] as they imply a system of $4\pi$ electrons (diene) and a system of $2\pi$ electrons (dienophile). The reaction products are substituted cyclohexanes. The dienophile can also contain double bonds between carbon and another atom (for example an oxygen), with the formation of heterocyclic rings.

The mechanism is almost certainly concerted and in a single step: both of the new carbon-carbon bonds are partially formed in the same transition state, even if not necessarily in the same extent. The Diels-Alder reaction is not only useful because it forms a cyclic compound, but above all because it takes place with great facility on a wide range of reagents. The reaction is favoured by the electron-attractor substituents in the dienophile, but simple alkenes can also react; the reaction often takes place with the production of heat by simple mixing of the reagents.

1,3-dipolar cycloadditions are cycloadditions which are thermodynamically permitted between a 1,3-dipole and a dipolarophile to form 5-atom aromatic heterocyclic rings, partially or totally saturated. 1,3-dipoles are compounds which can be described by octet or sextet zwitterionic forms and can be of the allyl type (angulated structure) or of the propargyl-allene type. 1,3-dipoles can have an N, O or S atom, as central atom. 1,3-dipoles with a nitrogen as central atom are the most important. Examples of nitrogen 1,3-dipoles of the propargyl (linear) type are azide, nitrilide, nitrilimine, nitriloxide, diazoalkane and nitrogen suboxide. The application of 1,3-dipolar cycloaddition reactions in the construction of isoxazole and pyrazole rings is particularly important due to their regioselectivity (generally total) and stereospecificity (G. A. Pagani, A. Abbotto, "Chimica Eterociclica", Ed. Piccin).

Among these types of reactions, Huisgen [3+2] 1,3-dipolar cycloaddition reactions are of particular interest (R. Huisgen et al., *Chem. Ber.* 1967, 100, 2494-2507): these are condensation reactions between organic azides and species having terminal alkyne groups which lead to the formation of a single derivative, rapidly and with a high yield, characterized by a bisubstituted 1,2,3-triazole ring (R, Huisgen, *Pure Appl. Chem.* 1989, 61, 613-628). The above reaction generates a mixture of 1,4- and 1,5-bisubstituted triazole rings (see FIG. 1).

Various attempts were made for controlling the regioselectivity, until the discovery, in 2002, of the possibility of using copper (I) as reaction catalyst, which exclusively leads to the formation of the 1,4-bisubstituted 1,2,3-triazole ring (FIG. 2) (V. Rostovtsev, et al., *Angew. Chem. Int. Ed.,* 2002, 41, 2596-2599; C. W. TorØe et al., *J. Org. Chem.,* 2002, 67, 3057-3064; B. K. Sharples et al., WO 03/101972).

In this type of reaction, substituted primary, secondary and tertiary azides and also aromatic azides are used. Numerous compounds having alkyne terminal groups can be used in said reaction, which is not impaired by the presence of various functional groups such as esters, acids, alkenes, alcohols and amines.

The same type of reaction between azides and alkynes takes place under bland conditions in an aqueous environment also in the absence of a catalyst, when the alkyne has electron-attractor substituents (Z. Li et al., *Tetrahedron Letters,* 2004, 45, 3143-3146).

The practical importance of this reaction, which is particularly relevant within the field of so-called "click chemistry", derives from the easy insertion of the terminal azide groups and alkyne groups in a wide variety of organic molecules. These groups subsequently react with each other also in the presence of other species with various possible functionalities. This prerogative has proved to be particularly advantageous in numerous sectors, from drug discovery to surface science, in which the formation of new bonds, and therefore new products, must be regioselective, rapid and must take place with high yields.

The Huisgen reaction, for example, has in fact been used in recent years for rapidly and effectively conjugating mono- and di-saccharides by means of bridges containing 1,2,3-triazole rings (S. Chittaboina et al., *Tetrahedron Letters,* 2005, 46, 2331-2336), to link functional groups, which would otherwise be difficult to introduce, to linear β-glucanes with the same method, (T. Hasegawa et al., *Carbohydrate Research,* 2006, 341, 35-40), for the regioselective synthesis with high yields of a wide range of dendrimers (V. Fokin et al., WO 2006/005046), for the coupling of macromolecules such as oligonucleotides and proteins with other molecular entities (W. Pieken et al., WO 98/30575), for the crosslinking of polyvinyl alcohols by means of linkers containing triazole groups (J. Ossipov et al., *Macromolecules,* 2006, 39(5), 1709-1718).

Although cycloaddition reactions are known as being common synthesis procedures for obtaining various types of chemical derivatives, the process according to the present invention envisages crosslinking by means of "click chemistry" reactions of polycarboxylated polysaccharides, in which at least one of the polysaccharide chains consists of suitably functionalized chains of hyaluronic acid or derivatives thereof—as also other uronanes and generic polycarboxylates—with the production of hydrogels with a known crosslinking degree which can be well modulated.

A particularly advantageous aspect of the process according to the present invention lies in the fact that the crosslinking reactions can be carried out in the presence of different molecules without the formation of undesired side-products, thus enabling, among other things, the production of new types of biocompatible materials and the incorporation, directly in the formation phase of the hydrogel, of various types of bioactive molecules, as well as cellular material, in matrices for release systems and in medicated gels for reconstructive surgery or for gene therapy.

Figure 4:
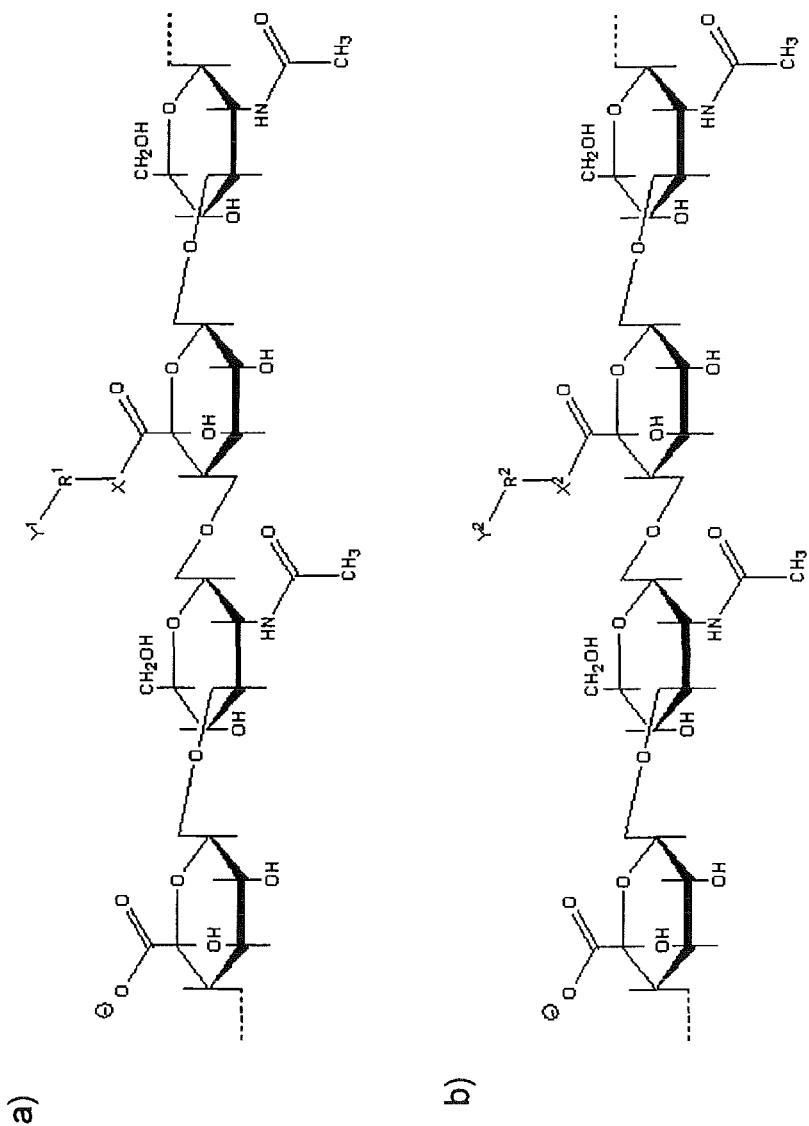
FIG. 4: Polysaccharide derivatives where both of the polysaccharide blocks consist of hyaluronate, suitably functionalized at the level of some of its carboxylic groups, but one of the two blocks could also be represented by a different polycarboxylated polysaccharide analogously modified.

In the structures of FIG. 4, the X1, R1 and Y1 groups are thus defined:

X1 and X2 can independently be O, NH, OC(O), S groups (i.e. the derivative of carboxylic acid can be an ester, an amide, an anhydride, a thioester, respectively);

R1 and R2 can independently be substituted or non-substituted aliphatic chains with a number of carbon atoms varying from 1 to 20, possibly containing heteroatoms, or groups of the aromatic, arylaliphatic, cyclo-aliphatic, heterocyclic series, in particular other triazole groups, and they can also contain or be derivatives of bioactive molecules;

Y1 and Y2 are residues containing groups capable of reacting with each other in a cycloaddition reaction belonging to the range of "click chemistry", as defined according to the present patent application, and preferably residues containing groups capable of reacting with each other in a Diels Alder cycloaddition or a 1,3-dipolar cycloaddition. More specifically, the pair (Y1, Y2) is a pair of the (1,3-unsaturated, dienophile), or (1,3-dipole, dipolarophile) type, wherein: —the 1,3-unsaturated compound is selected from derivatives of 1,3-dienes (also called conjugated dienes), and preferably from 1,3-butadiene, 1-methoxy-3-trimethylsilyloxy-1,3-butadiene, cyclopentadiene, cyclo-hexadiene, furan, —the dienophile compound is selected from alkenes, alkynes or derivatives of alkenes or alkynes with one or more electron-attractor groups linked to the double or triple bond, and preferably from acrylates, acrylamides, fumarates, vinylketones, nitro-alkenes, nitro-alkynes, maleic anhydride and quinones;

the 1,3-dipole compound is selected from derivatives of nitrile-oxides, azides, diazo-alkanes, allenes and nitrones, and preferably from derivatives of azides;

the dipolarophile compound is selected from alkenes, alkynes or from derivatives of alkenes or alkynes with one or more electron-attractor groups bound to the double or triple bond, and preferably from acrylates, acrylamides, fumarates, vinylketones, nitro-alkenes, nitro-alkynes, maleic anhydride, methylacetylene and quinones.

Figure 5:

FIG. 5: A photograph of a hydrogel obtained by crosslinking of hyaluronic acid chains by means of Huisgen cycloaddition.

Figure 6:
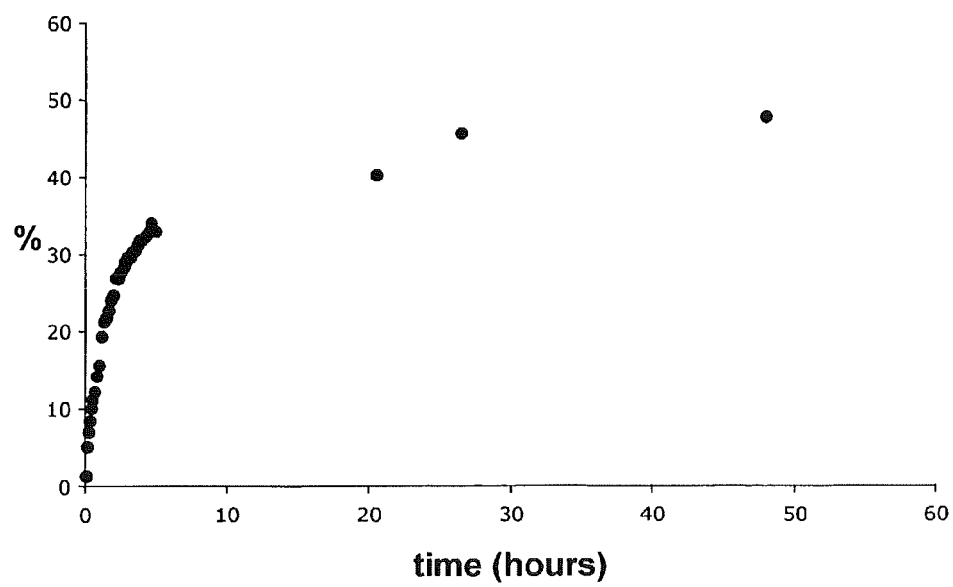

FIG. 6: Graph of the release of doxorubicin hydrochloride from the matrices of the hydrogels obtained after crosslinking over about 50 h.

Figure 7:
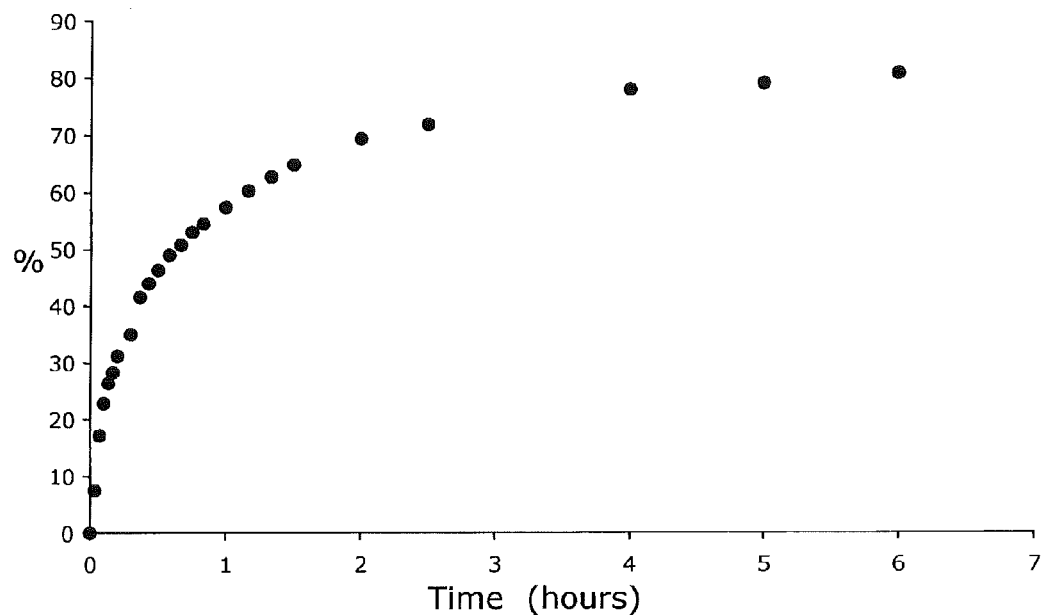

FIG. 7: Graph of the controlled release of benzy-damine hydrochloride.

Figure 8:
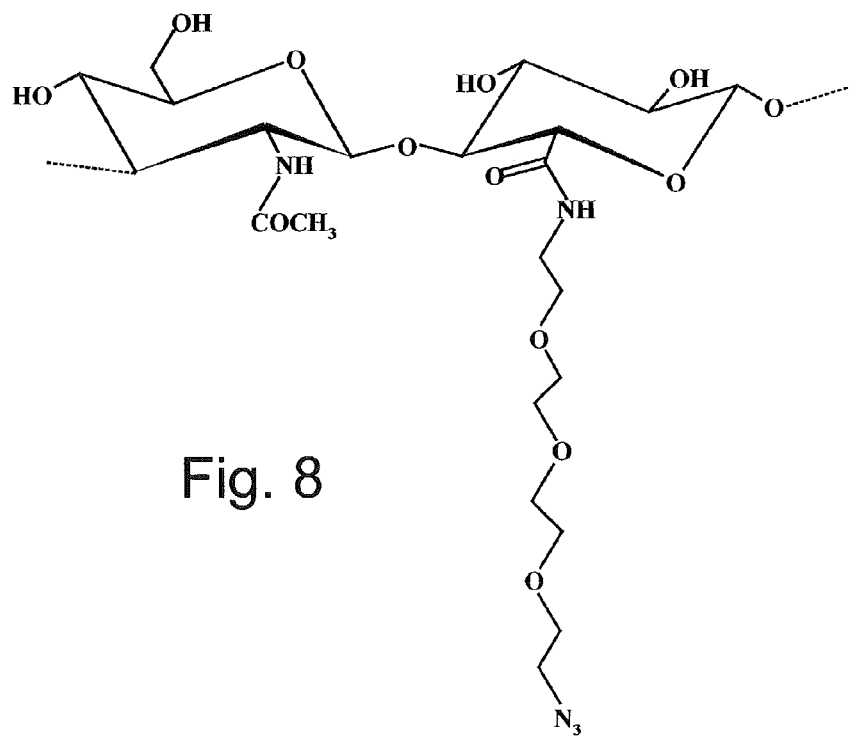

FIG. 8: Structure of Product 1.

Figure 9:
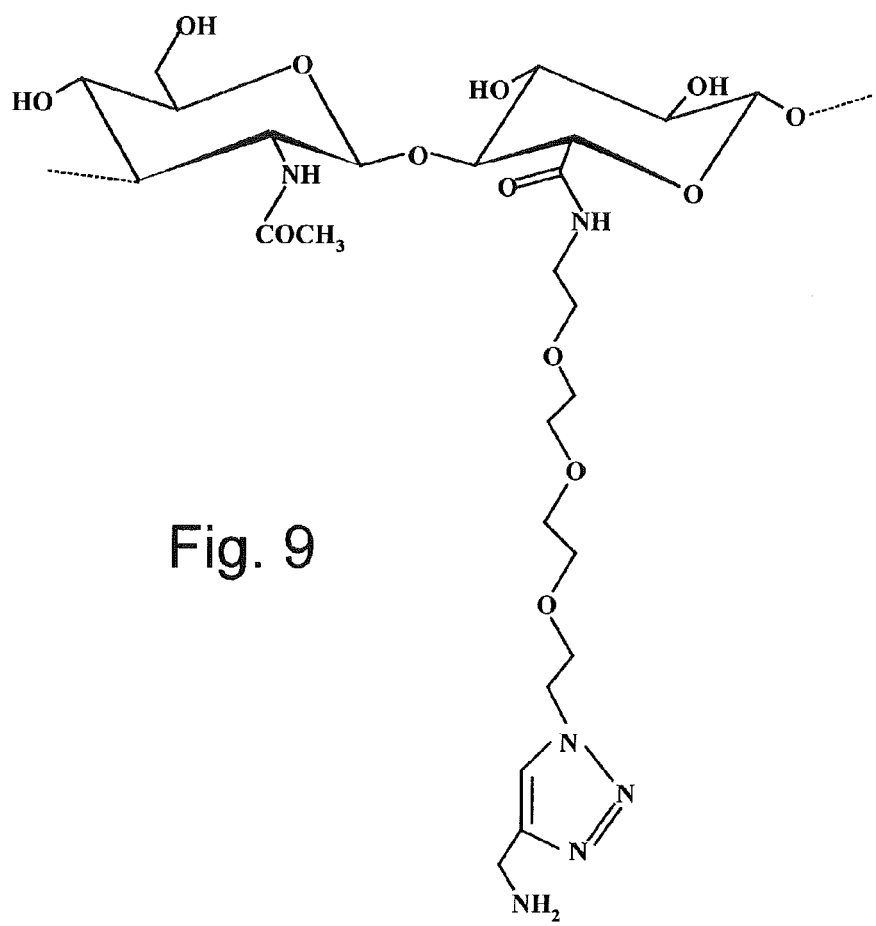

FIG. 9: The structure obtained by the reaction of Product 1 with propargylamine.

Figure 10:
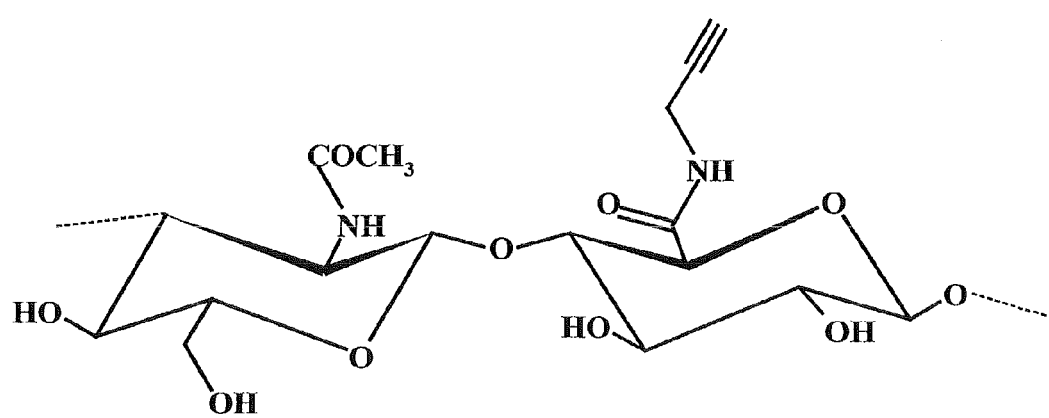

FIG. 10: The structure of Product 2.

Figure 11:
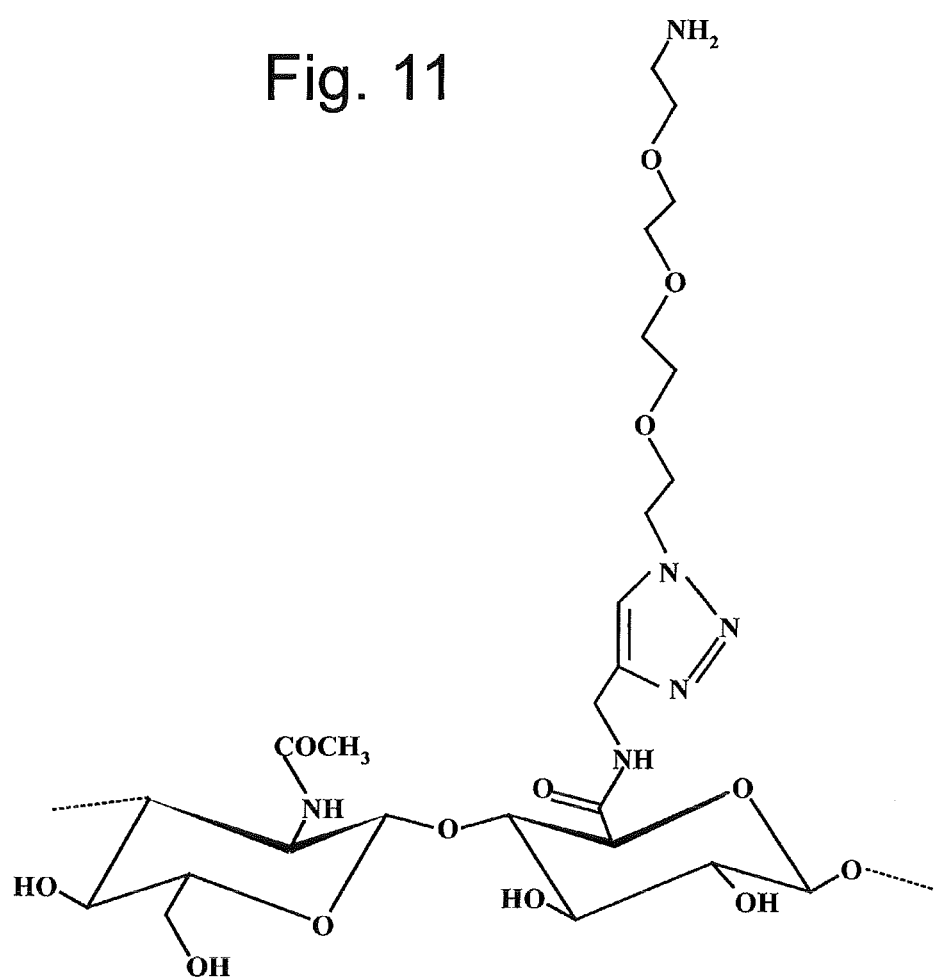

FIG. 11: The structure obtained by the reaction of Product 2 with II-azide-3,6,9,-trioxaundecane-1-amine.

Figure 12:
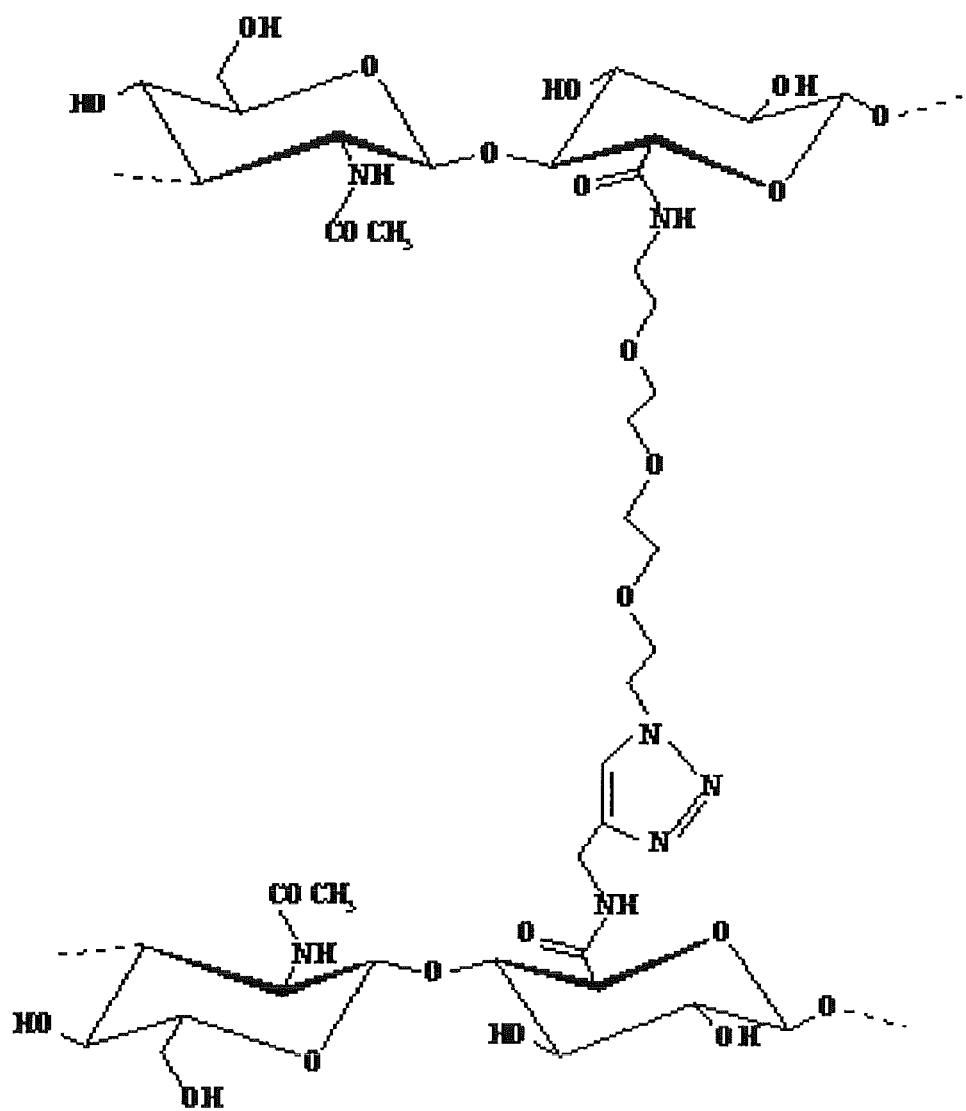

FIG. 12: The structure of a hydrogel.

Figure 13:
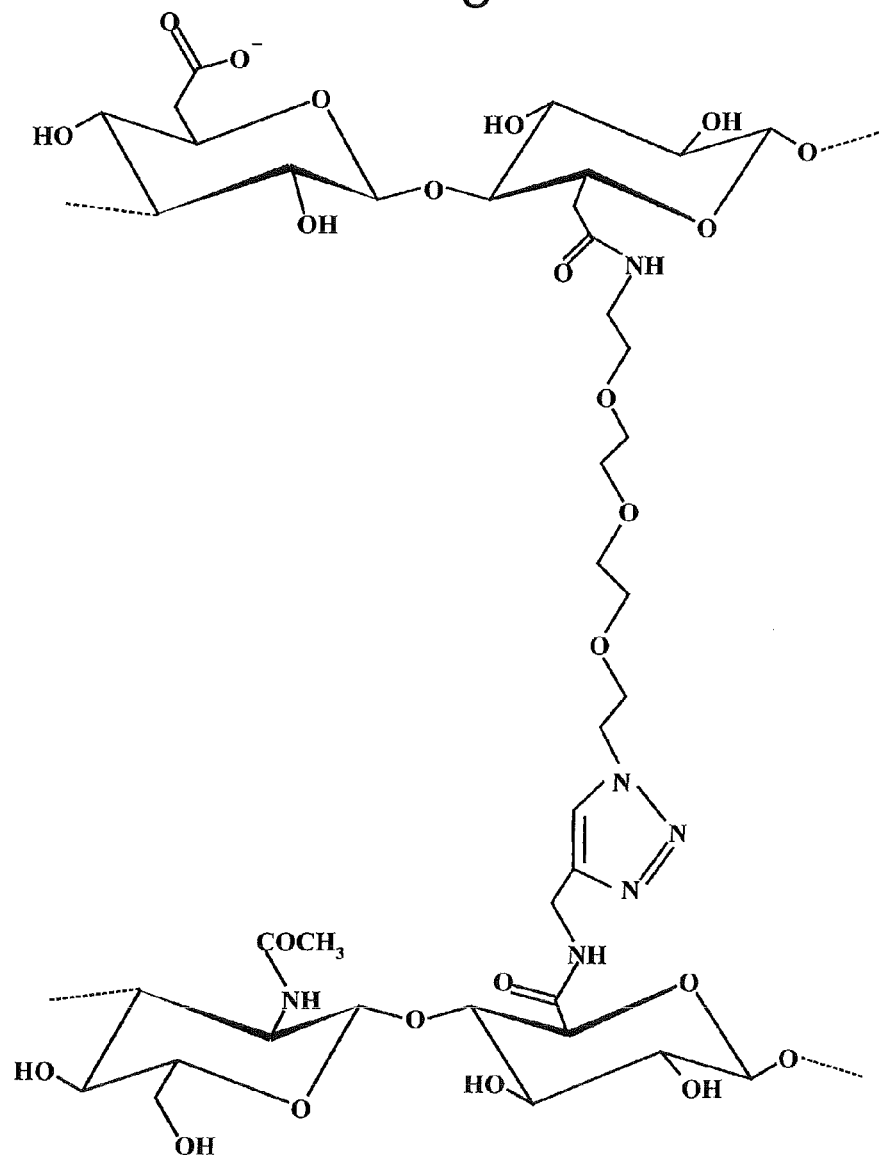

FIG. 13: The structure of a hydrogel of hyaluronic acid and carboxymethylcellulose in an aqueous solvent.

Figure 14:
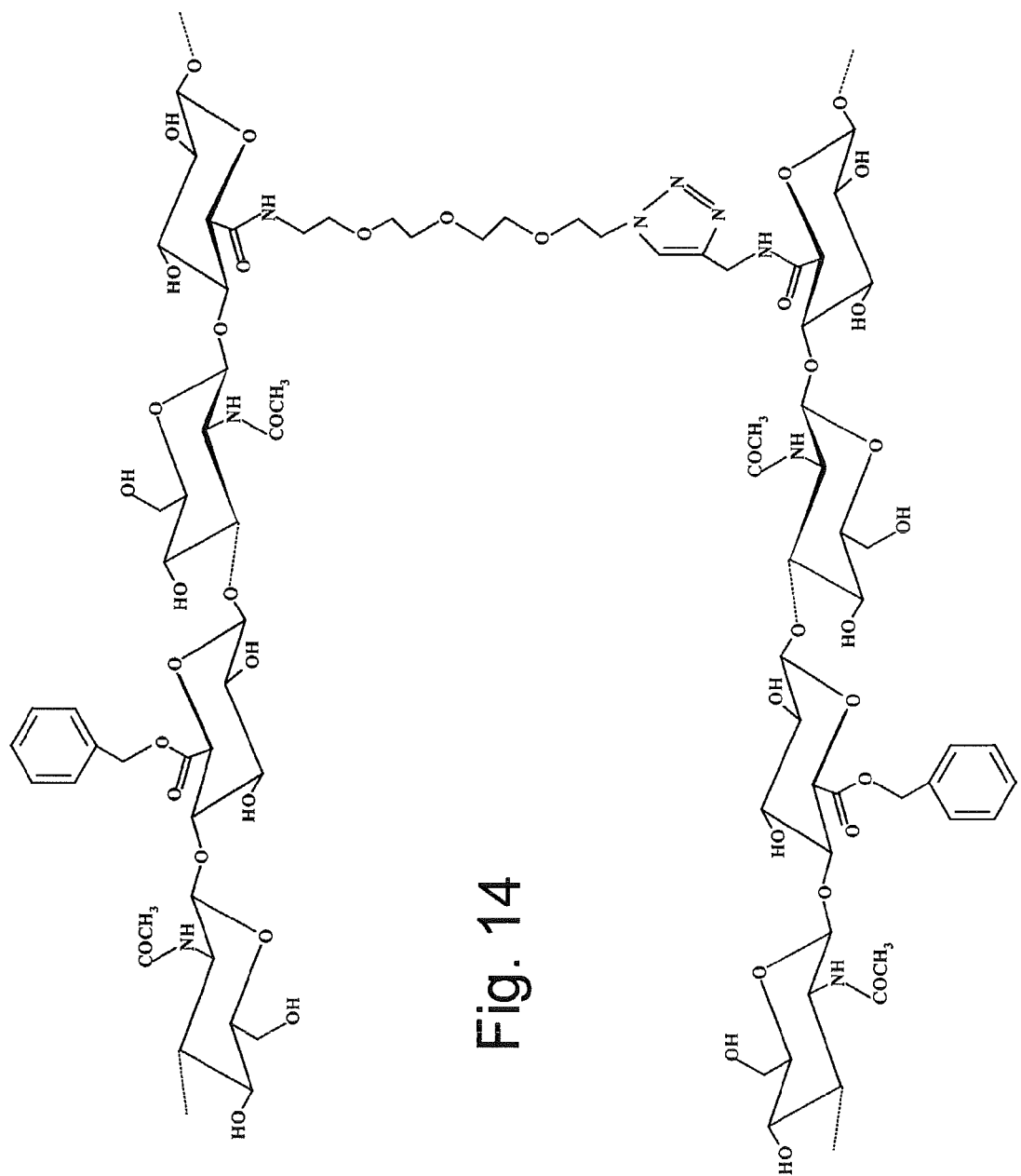

FIG. 14: The structure of a gel obtained by the Amidation of Hyaffllp50 with propargylamine in an aqueous solvent at pH=4 in the presence of EDC.HCl and NHS.

Figure 15:
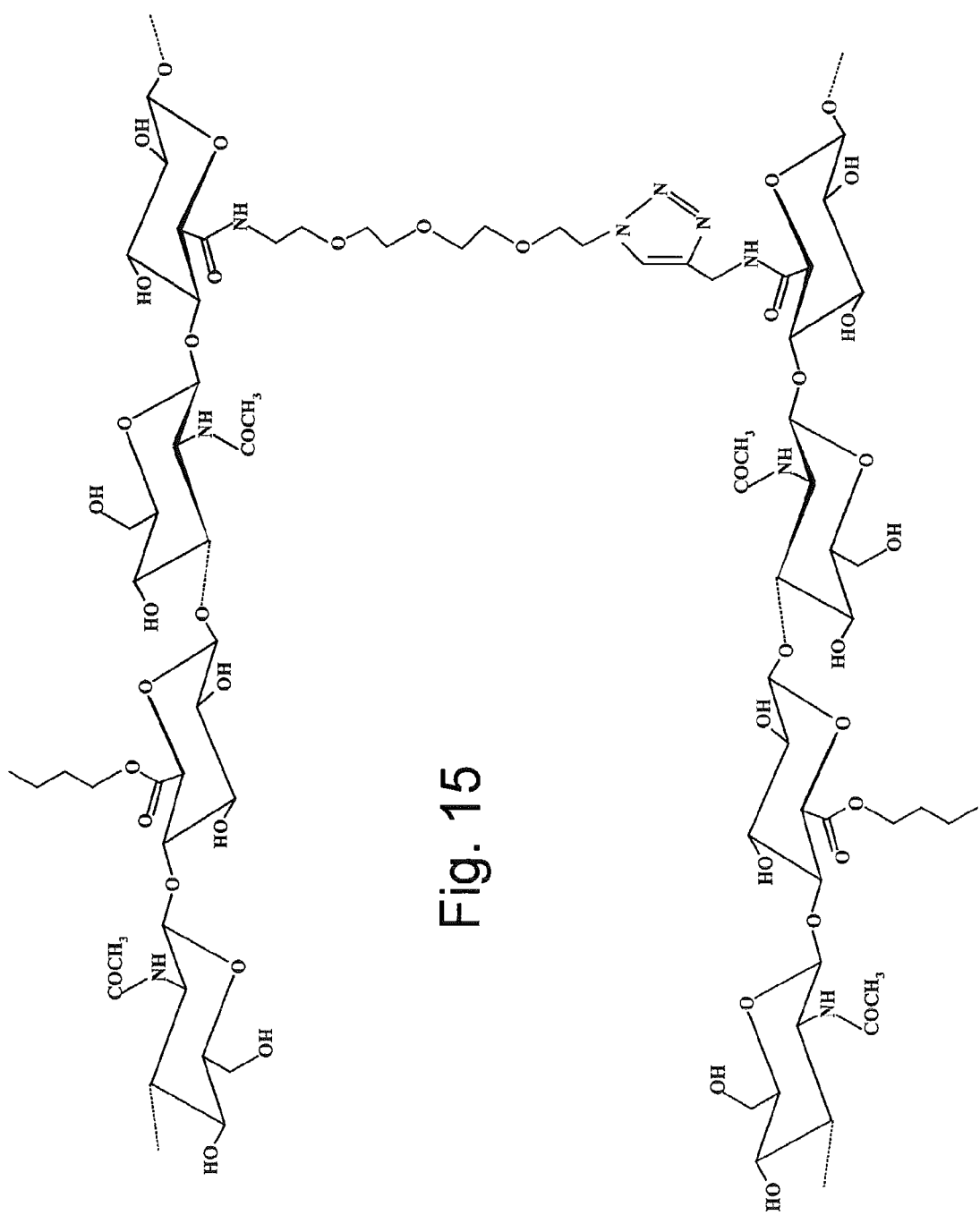

FIG. 15: The structure of a gel obtained by the formation of the hydrogel of Hyaff9p10 in an aqueous solvent.

Figure 16:
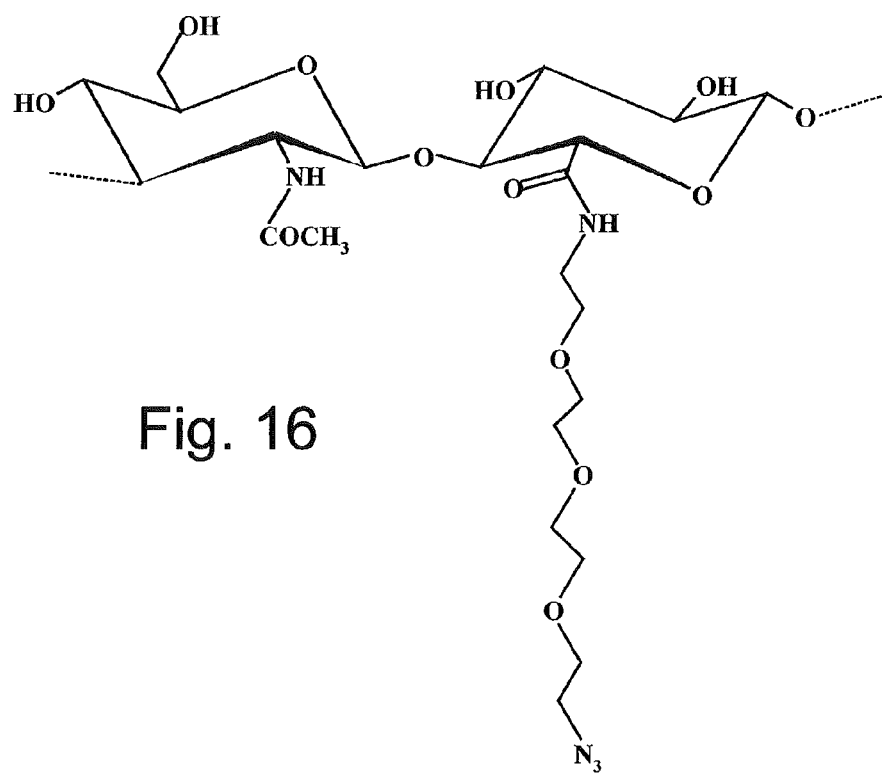

FIG. 16: The structure of Product 1 obtained by the Amidation of HANa with 11-azide-3,6,9-trioxaundecane-1-amine in an aqueous solvent at pH=4 in the presence of EDC.HCl and NHS.

Figure 17:
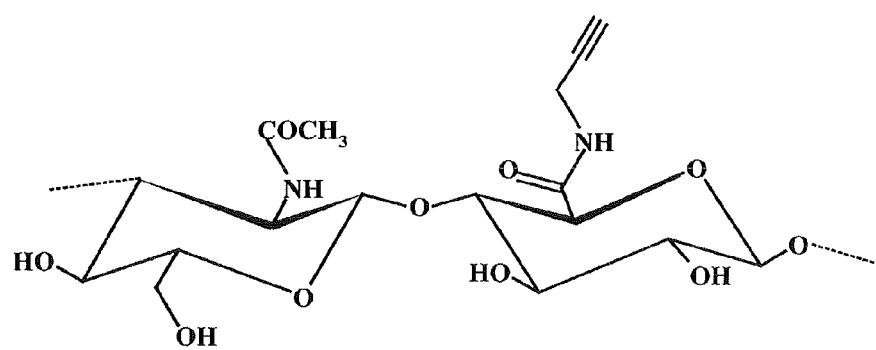

FIG. 17: The structure of Product 2 obtained by the Amidation of HANa with propargylamine in an aqueous solvent at pH=4 in the presence of EDC.HCl and NHS.

Figure 18:
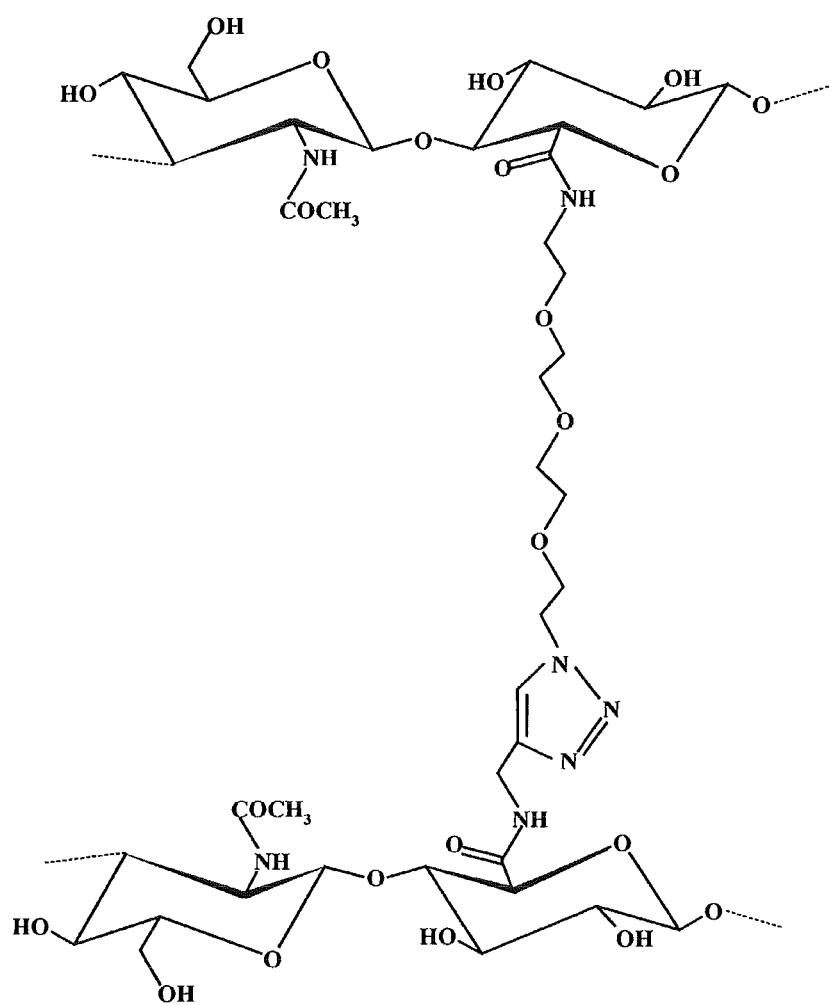

FIG. 18: The structure hydrogel of hyaluronic acid formed with catalytic $CuSO_4 * 5H_2O$ and ascorbic acid in an aqueous solvent in the present of BSA.

Figure 19:
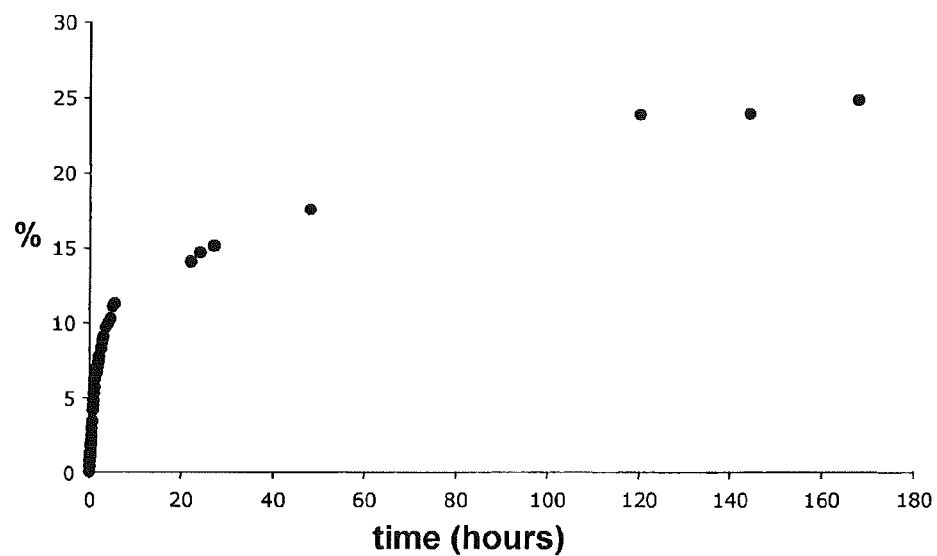

FIG. 19: A graph of the release measurements of the drug doxorubicin hydrochloride from hydrogels based on crosslinked hyaluronic acid obtained with catalytic CuCl.

Figure 20:
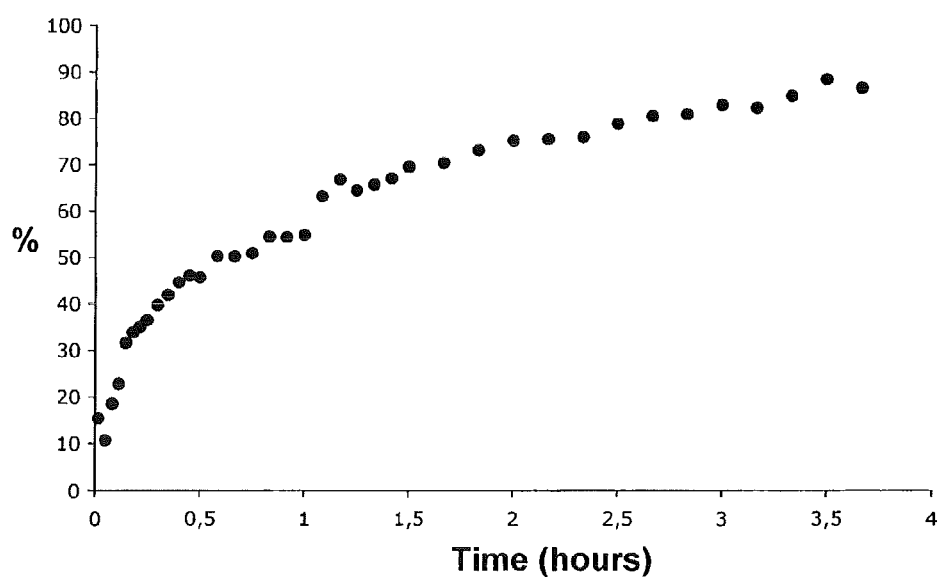

FIG. 20: A graph of the release measurements of the drug benzydamine hydrochloride from hydrogels based on crosslinked hyaluronic acid obtained with catalytic CuCl.

Figure 21:
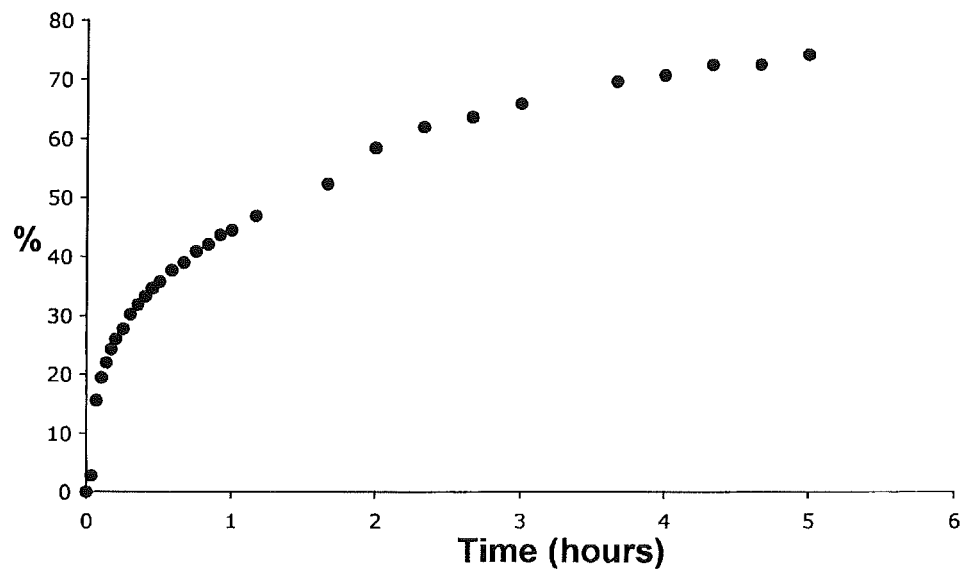

FIG. 21: A graph of the release measurements of the drug benzydamine hydrochloride from hydrogels based on crosslinked hyaluronic acid obtained with catalytic $CuSO_4.5H_2O$.

Figure 22:
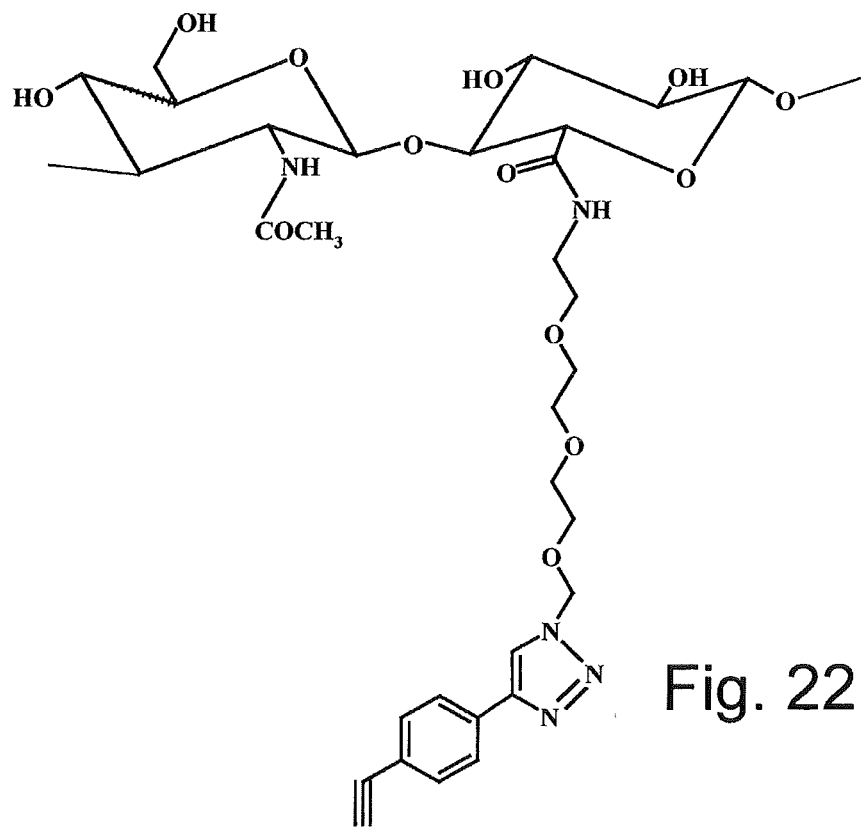

FIG. 22: Structure of the product obtained by the reaction of product 1 with 1,4-Diethynylbenzene in an aqueous/organic solvent with catalytic $CuSO_4 * 5H_2O$ and ascorbic acid.

Figure 23:
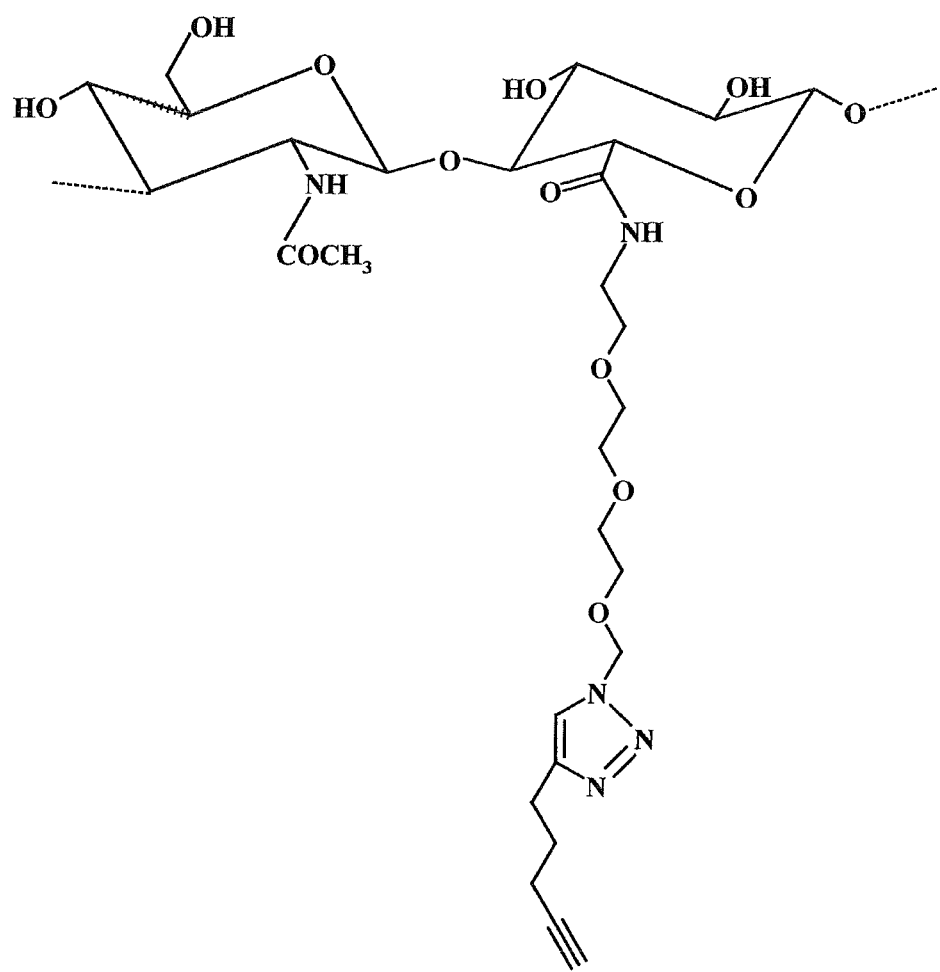

FIG. 23: Structure of the product obtained by the reaction of product 1 with 1,6-Heptadiyne in an aqueous/organic solvent with catalytic $CuSO_4 * 5H_2O$ and ascorbic acid.

Figure 24:
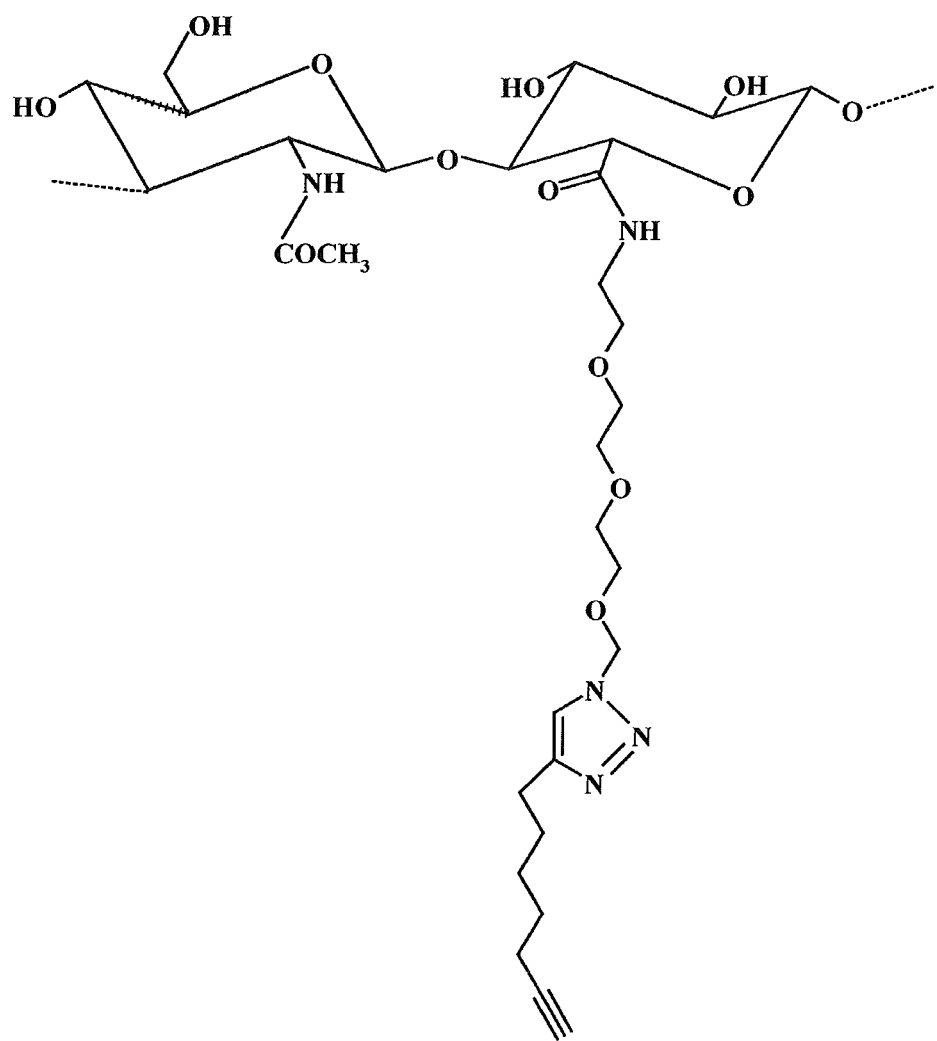

FIG. 24: Structure of the product obtained by the Reaction of product 1 with 1,8-Nonadiyne in an aqueous/organic solvent with catalytic $CuSO_4 * 5H_2O$ and ascorbic acid.

Figure 25:
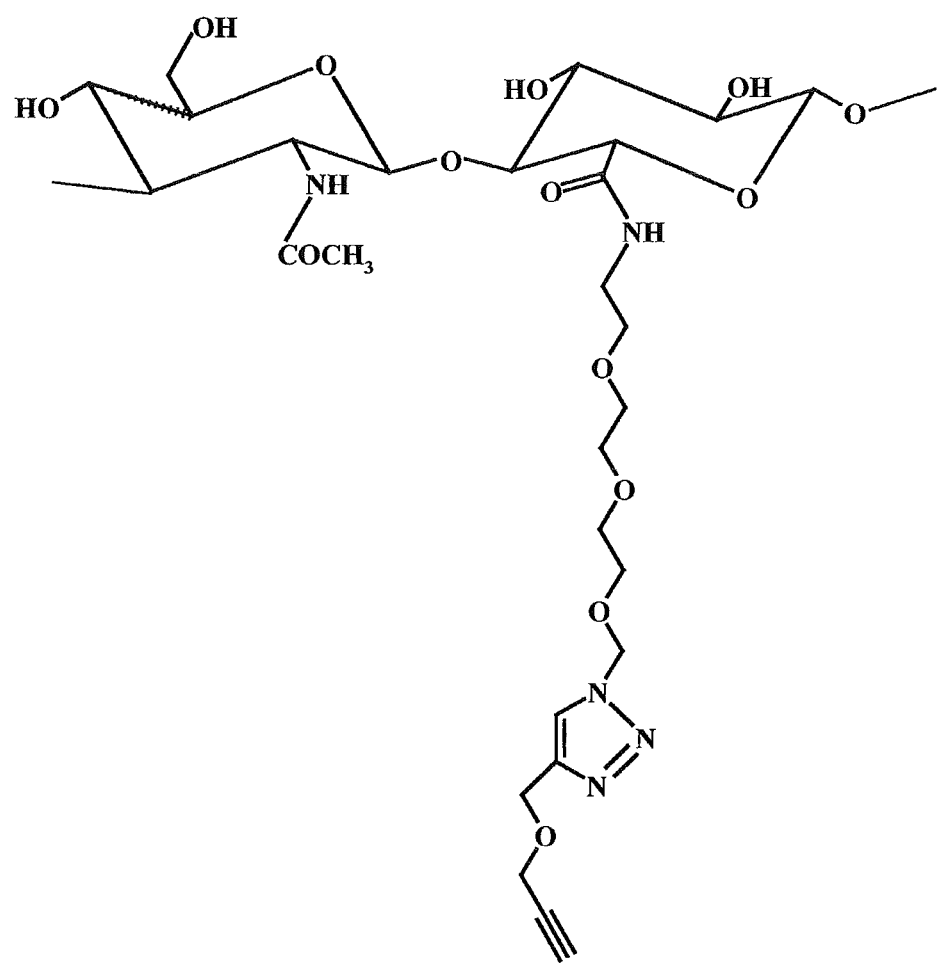

FIG. 25: Structure of the product obtained by the reaction of product 1 with propargyl ether in an aqueous/organic solvent with catalytic $CuSO_4 * 5H_2O$ and ascorbic acid.

Figure 26:
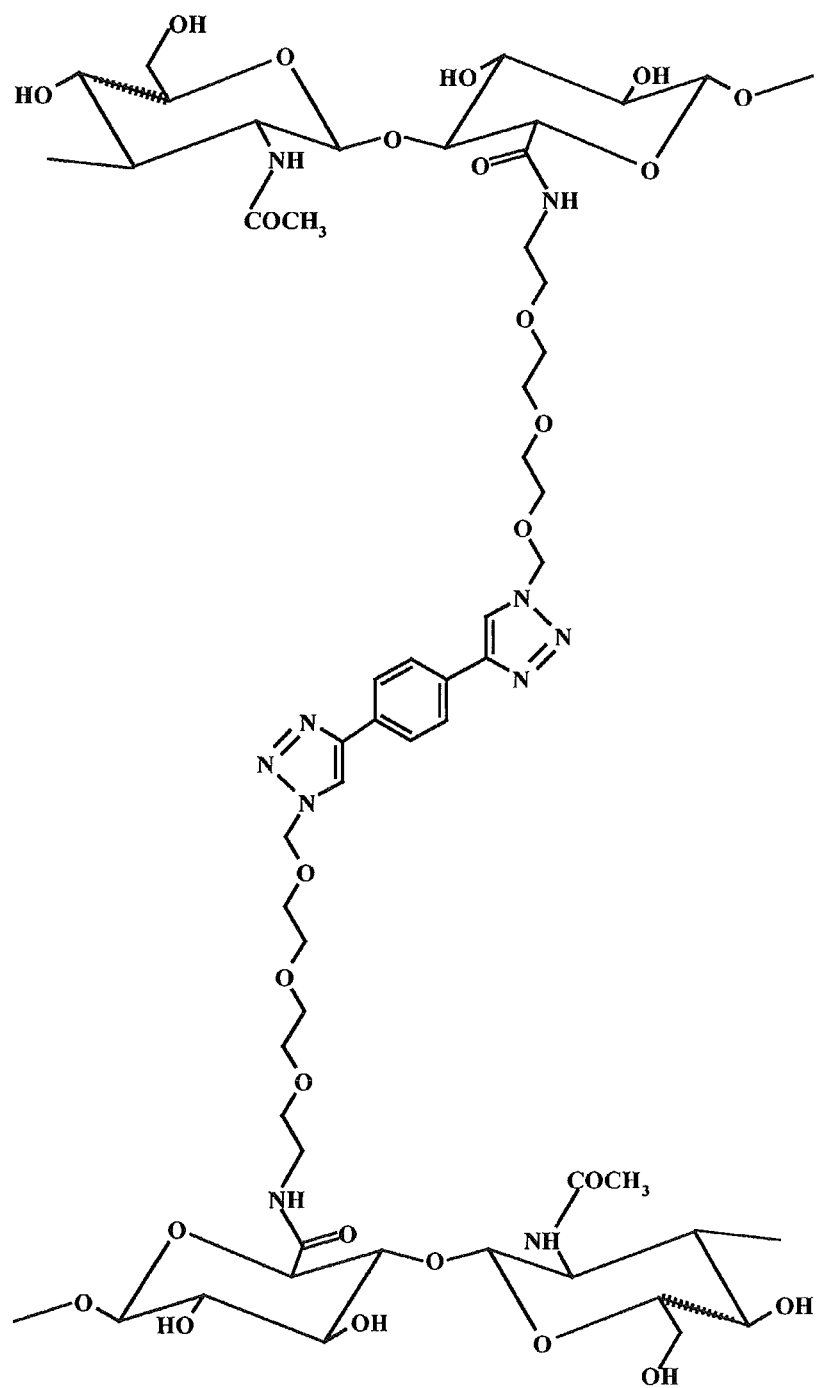

FIG. 26: Structure of the hydrogel formed by the reaction of hyaluronic acid with 1,4-Diethynylbenzene obtained with catalytic $CuSO_4 * 5H_2O$ and ascorbic acid in an aqueous/organic solvent in the presence of doxorubicin hydrochloride.

Figure 27:
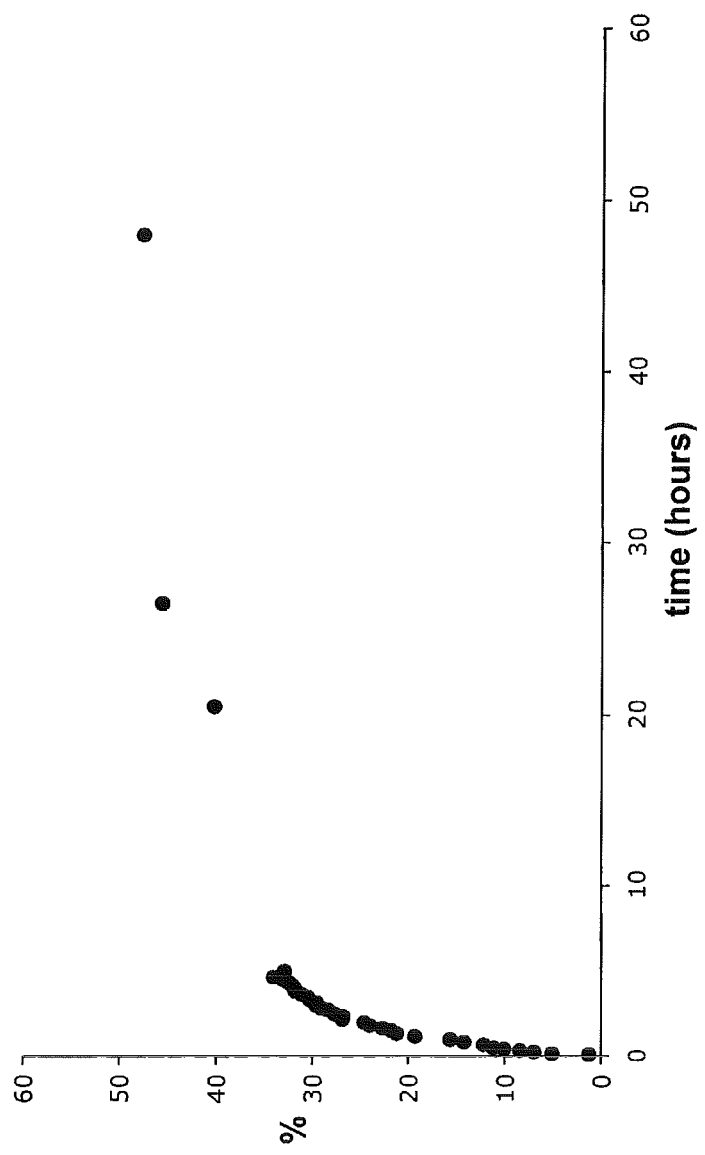

FIG. 27: A graph of release measurements of the drug doxorubicin hydrochloride from a hydrogel based on hyaluronic acid with 1,4-diethynylbenzene obtained with catalytic $CuSO_4 \cdot 5H_2O$ and ascorbic acid in an aqueous/organic solvent.

Figure 28:
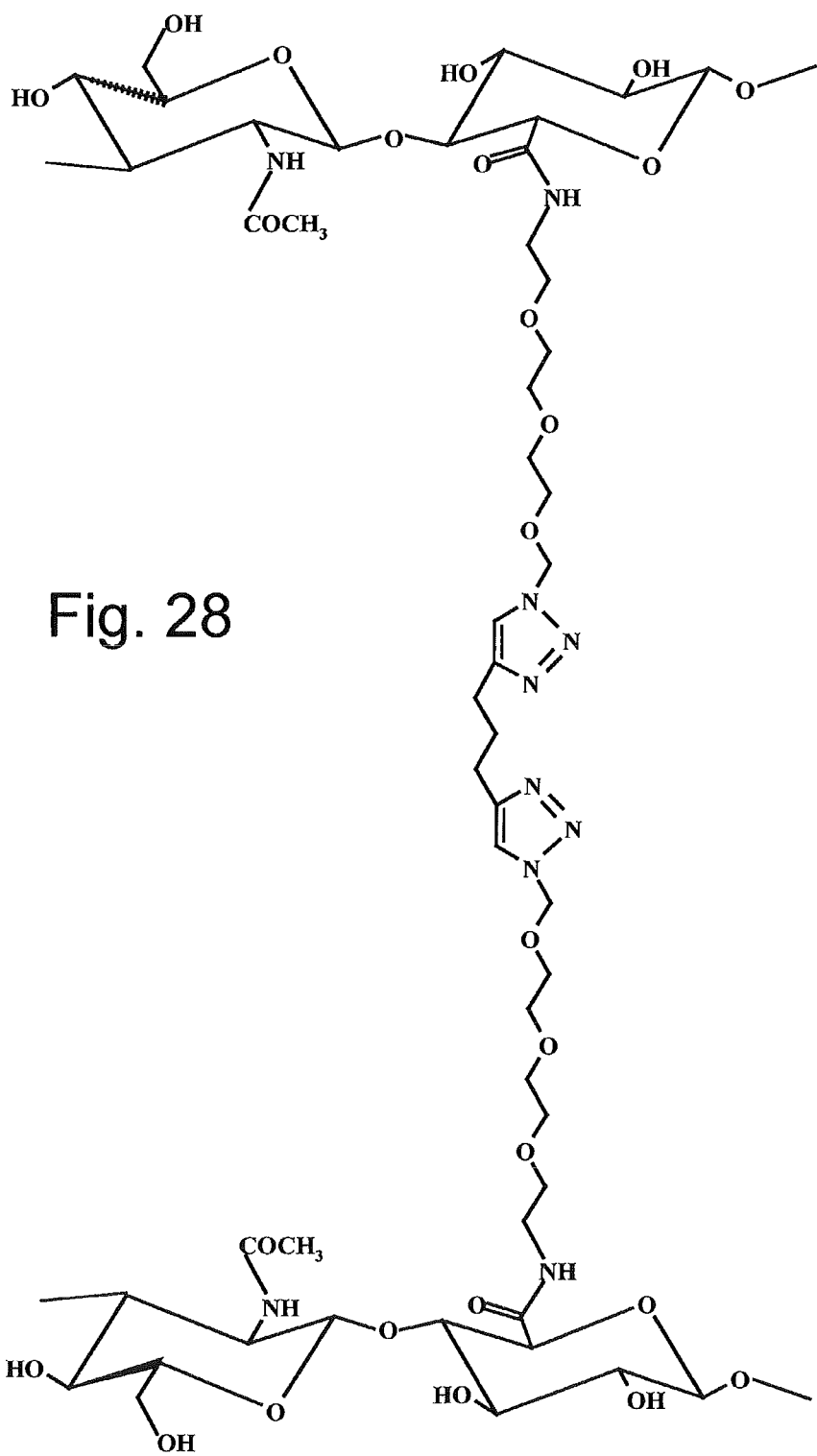

FIG. 28: Structure of the hydrogel formed by the reaction of hyaluronic acid with 1,6-Heptadiyne obtained with catalytic $CuSO_4 \cdot 5H_2O$ and ascorbic acid in an aqueous/organic solvent in the presence of doxorubicin hydrochloride.

Figure 29:
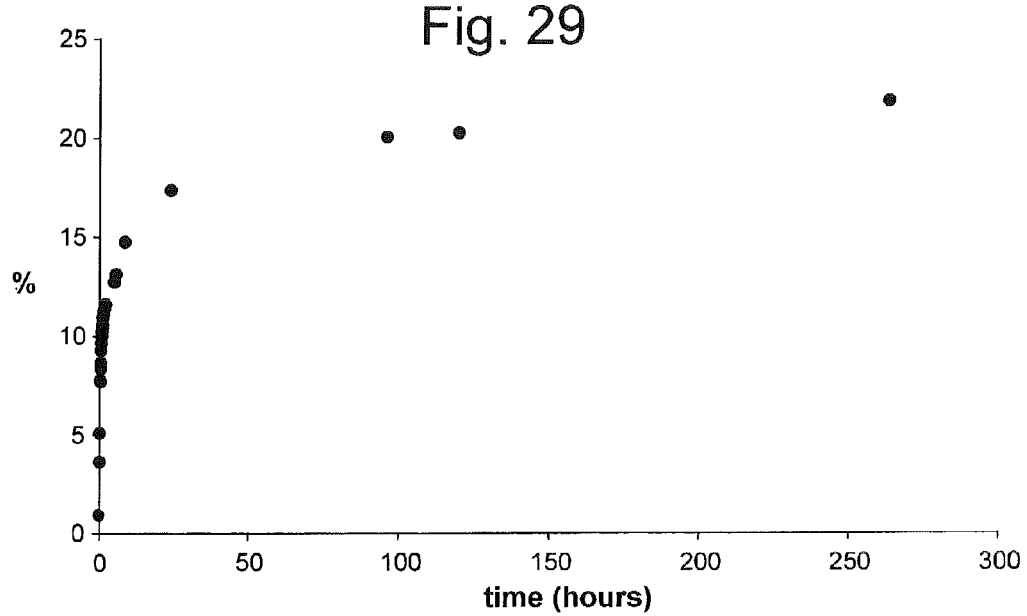

FIG. 29: A graph of release measurements of the drug doxorubicin hydrochloride from a hydrogel based on hyaluronic acid with 1,6-heptadiyne obtained with catalytic $CuSO_4 \cdot 5H_2O$ and ascorbic acid.

Figure 30:
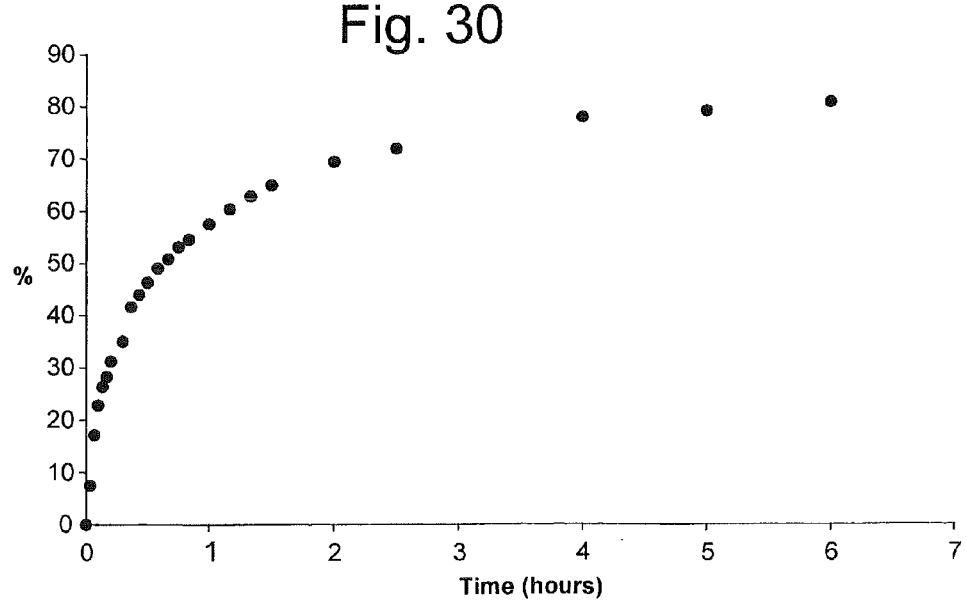

FIG. 30: A graph of release measurements of the drug benzydamine hydrochloride from a hydrogel based on hyaluronic acid with 1,6-Heptadiyne obtained with catalytic $CuSO_4 \cdot 5H_2O$ and ascorbic acid.

Figure 31:
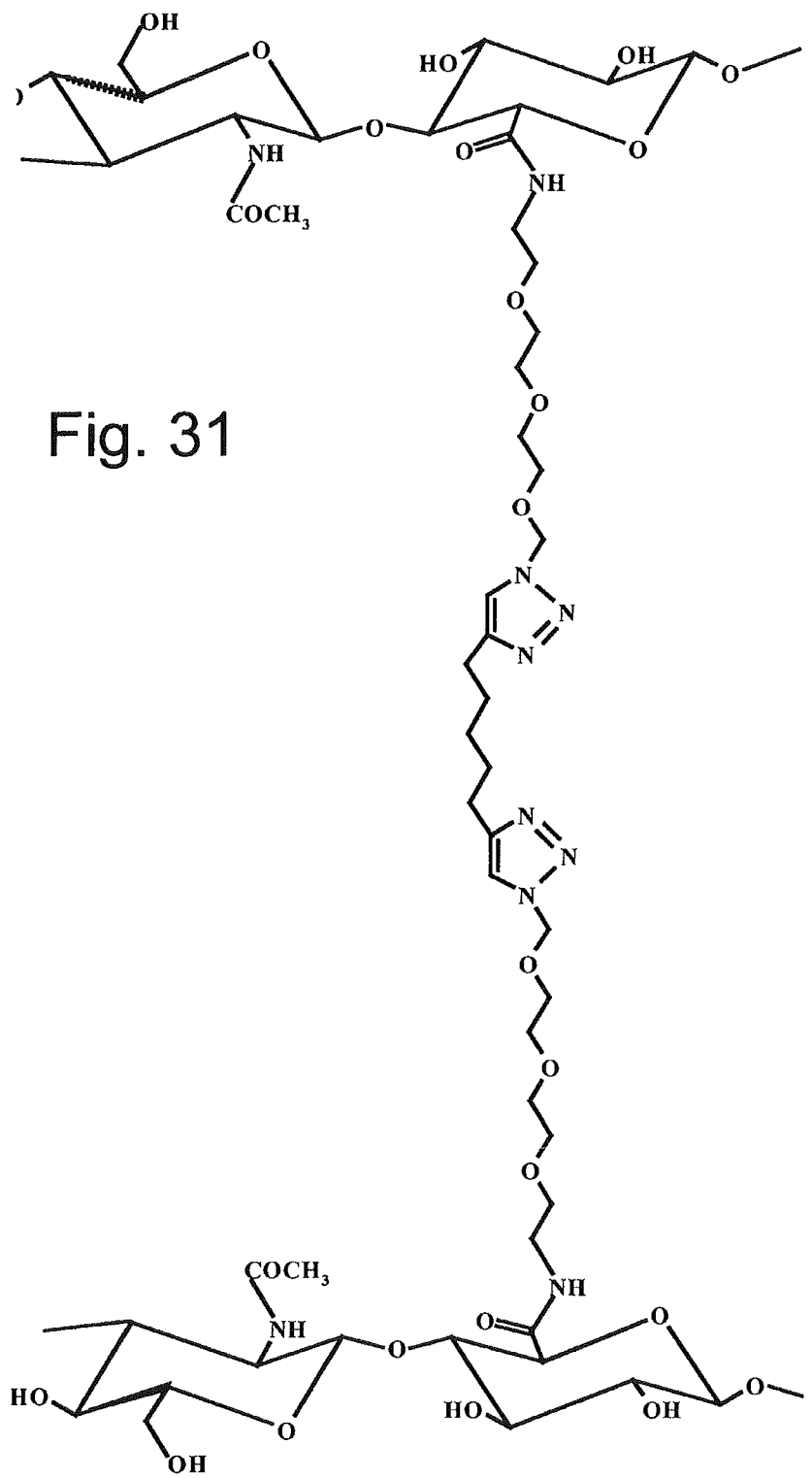

FIG. 31: Structure of the hydrogel formed by the reaction of hyaluronic acid with 1,8-Nonadiyne obtained with catalytic $CuSO_4 \cdot 5H_2O$ and ascorbic acid in an aqueous/organic solvent in the presence of doxorubicin hydrochloride.

Figure 32:
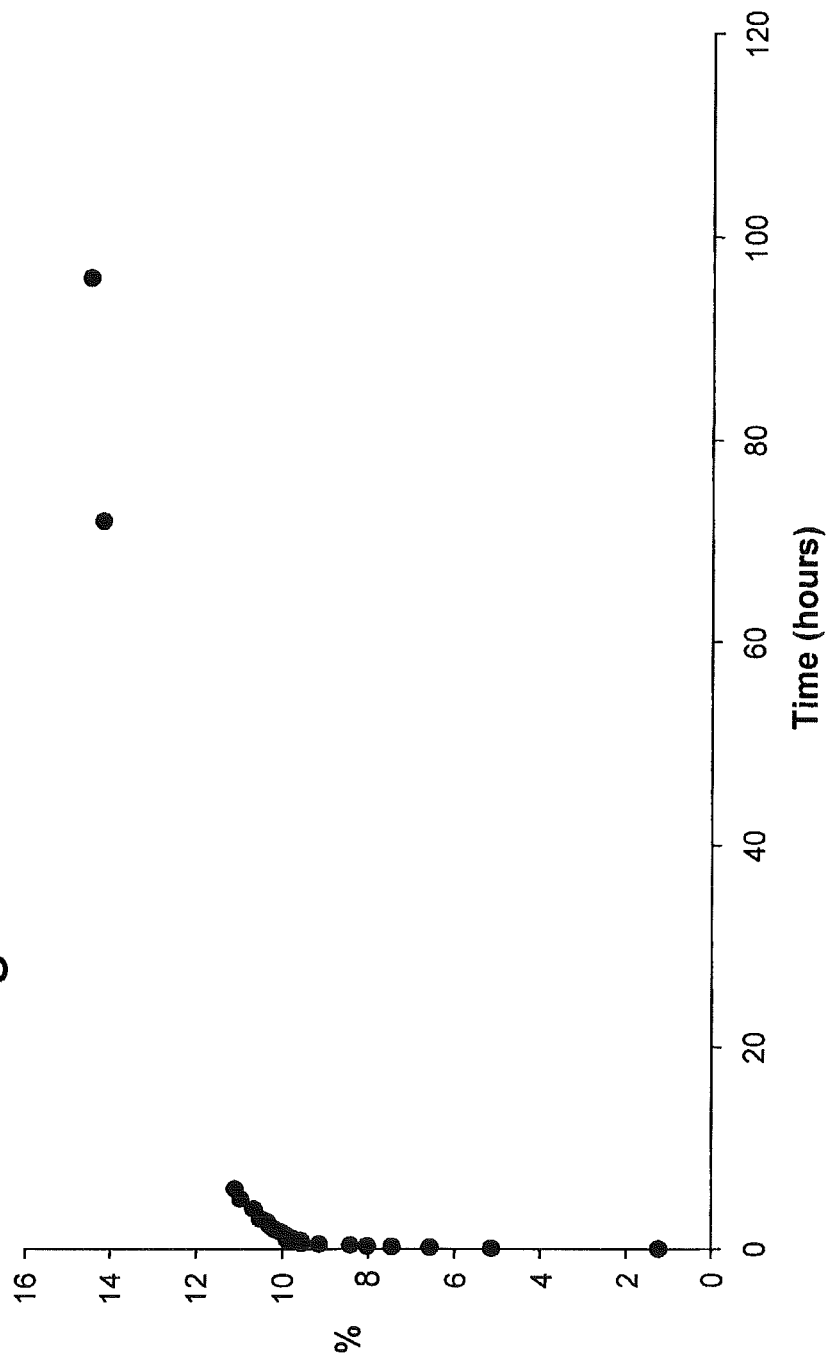

FIG. 32: A graph of the release measurements of the drug doxorubicin hydrochloride from a hydrogel based on hyaluronic acid with 1,8-Nonadiyne obtained with catalytic $CuSO_4 \cdot 5H_2O$.

DETAILED DESCRIPTION OF THE INVENTION

The present invention relates to a process for the preparation of crosslinked derivatives of polycarboxylated polysaccharides, wherein at least one of the polysaccharide chains consists of hyaluronic acid or a derivative thereof, crosslinked by means of "click chemistry"-type reactions, said process comprising the following phases:
  i) synthesis of partial derivatives (esters, amides, thioesters, anhydrides) of hyaluronic acid, and optionally another polycarboxylated polysaccharide or the respective salts or derivatives;
  ii) cycloaddition reaction between the derivatives obtained in phase i) with the formation of covalent bonds between the chains.

An object of the present invention also relates to crosslinked derivatives of polycarboxylated polysaccharides, wherein at least one of the polysaccharide chains consists of hyaluronic acid or a derivative thereof, crosslinked by means of reactions of the "click chemistry" type.

"Click chemistry" reactions are rapid and effective cycloaddition reactions between the same polysaccharide chains previously modified so as to introduce terminal functional groups subsequently involved in said reaction.

An object of the present invention also relates to said crosslinked polysaccharides in the form of hydrogels and their use in the medical field, in particular in viscosupplementation, plastic, oncologic and reconstructive surgery, as matrices for gene therapy and as matrices for controlled release systems of molecules and/or macromolecules with a biological or pharmacological activity, and also as biomaterials and supports for cellular material for use in tissue engineering or regeneration.

An object of the present invention also relates to controlled release systems of molecules and/or macromolecules with a biological or pharmacological activity, comprising as matrix the crosslinked derivatives in the form of hydrogels. In particular an object of the present invention also relates to controlled release systems of oligo- and poly-nucleotides for use in gene therapy, comprising as matrix the crosslinked derivatives in the form of hydrogels.

The crosslinked derivatives, object of the present invention—and the hydrogels obtained therefrom—can be prepared in an aqueous solvent by means of simple, rapid reactions with high yields belonging to the so-called "click chemistry" domain, thanks to the easy derivatization of hyaluronic acid (and derivatives thereof) and/or other polycarboxylated polysaccharides with molecules having reactive terminal groups in one of the "click" reactions, such as azides, alkynes, dienes, alkenes, nitrile oxides, diazoalkanes. It has also been surprisingly found that during the formation reaction of these polysaccharide derivatives and hydrogels, other molecules having numerous types of functional groups different from those mentioned above, can be present in the reaction mixture without forming undesired side-products and without influencing the rate, yield and possible regioselectivity of the cycloaddition reaction. This means that a wide range of simple bioactive molecules, peptides, proteins, oligo- and poly-nucleotides, and other polymers can be physically incorporated in the hydrogels object of the present invention directly during their preparation process.

In particular, the materials thus obtained are characterized by a good biocompatibility, as they derive from polysaccharides which are biocompatible and degradable in the organism with the restoration of the same polysaccharides and molecules having a low toxicity or even, as in the case of triazoles, an antibacterial activity. The hyaluronic acid which can be used in the present invention can derive from any source, for example by extraction from chicken combs (EP 138572), or by fermentation (EP 0716688), and can have a molecular weight ranging from 400 to 3,000,000 Da, in particular, from 50,000 to 1,000,000 Da.

The derivatives of hyaluronic acid which can be used in the preparation of the intermediates necessary for the preparation of the crosslinked derivatives, object of the present invention, are the following:
  1) salts with organic and/or inorganic bases, also biologically active ones (EP 138572 B1);
  2) HYAFF®: esters of hyaluronic acid with alcohols of the aliphatic, araliphatic, cyclo-aliphatic, aromatic, cyclic and heterocyclic series, with an esterification percentage which can vary according to the type of alcohol and length of the alcohol used, but not higher than 90%, as the polymer must be still hydrosoluble and must include free carboxylic groups (EP 0216453 B1);
  3) HYADD®: amides of hyaluronic acid with amines of the aliphatic, araliphatic, cyclo-aliphatic, aromatic, cyclic and heterocyclic series, with an amidation percentage not higher than 50%, as the polymer must be still hydrosoluble (EP 1095064 B1);
  4) bioconjugated products obtained by direct or indirect synthesis (via molecular spacer) between hyaluronic acid or its derivatives and drugs with an antitumoral activity belonging to different families (Italian patent application PD2005A000242);
  5) O-sulfated derivatives (EP0702699 B1) and N-sulfated derivatives of hyaluronic acid (EP 0971961 A1);
  6) ACP®: internal esters of hyaluronic acid with an esterification percentage not higher than 20%, as the polymer must be still hydrosoluble (EP 0341745 B1);
  7) deacylated products of HA: the N-acetyl-glucosamine fraction is deacetylated with a deacetylation percentage preferably ranging from 0.1 to 30% (EP 1313772 B1);
  8) percarboxylated products of HA obtained from the oxidation of the primary hydroxyl of the N-acetyl-glucosamine fraction with a percarboxylation degree ranging from 0.1 to 100% (HYOXX® EP 1339753 A1)).

The free carboxylic groups of hyaluronic acid and its derivatives described above, which can be used in the crosslinking process according to the present invention, can be present in the form of carboxylic acids, carboxylated salts of cations of elements belonging to the group of alkaline or alkaline-earth metals, preferably sodium, potassium, magnesium and calcium, or carboxylated salts of tetra-alkylammonium ions, preferably tetrabutylammonium, benzalkonium, 2-chloro-1-methylpyridine and cetylpyridine.

Other natural or synthetic polycarboxylated polysaccharides which can be used for the preparation of the crosslinked derivatives, object of the present invention, are for example those belonging to the group of glycosaminoglycanes, and preferably chondroitins, sulfated dermatans, sulfated heparans and heparins (and their respective salts), as well as other natural polysaccharides such as alginic acid and salts thereof, and synthetic polysaccharides such as carboxymethylcellulose (CMC), hydroxypropylmethylcellulose (HPMC) and their salts.

Figure 1:
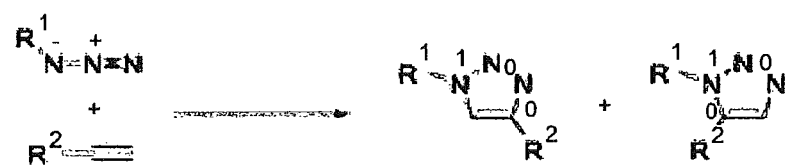
FIG. 1: A reaction to generate a mixture of 1,4- and 1,5-bisubstituted triazole rings.
Figure 2:
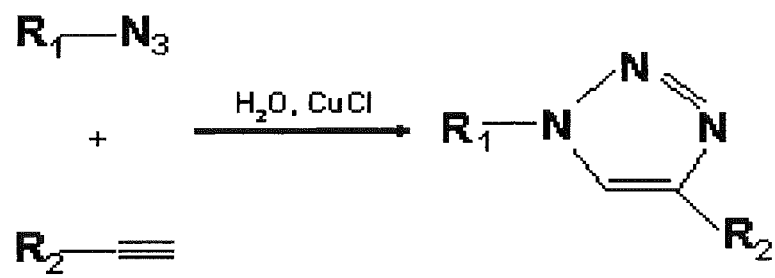
FIG. 2: "Click" Reaction scheme between an azide and alkyne.
Figure 3:
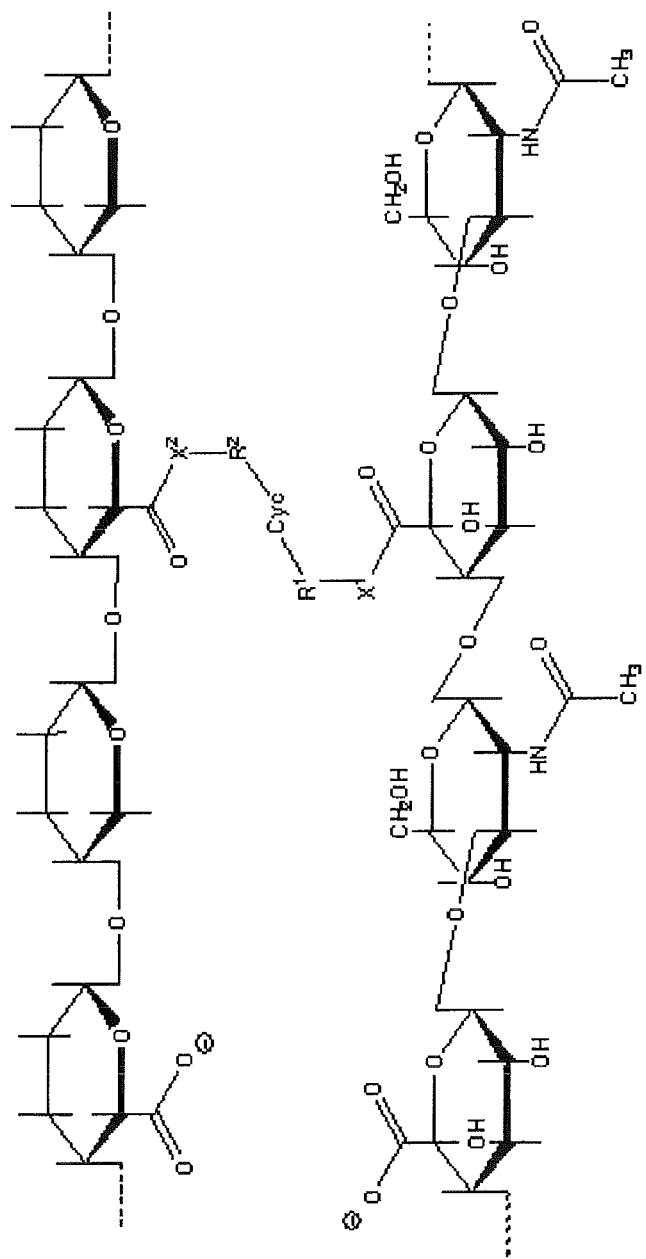
FIG. 3: Structures of the invention including derivatives of Hyaluronic acid having crosslinked polysaccharide structures.

The present invention therefore relates to derivatives having crosslinked polysaccharide structures as generally described in FIG. 3, wherein, as illustrated, at least one of the two chains involved in the crosslinking is hyaluronic acid, or one of its derivatives previously described (in this case hyaluronate is indicated for purely illustrative purposes), and the second chain can be the same or any other polycarboxylated polysaccharide, and wherein in order:

- $X^1$ and $X^2$ can independently be O, NH, OC(O), S groups (or the derivative of carboxylic acid can be an ester, an amide, an anhydride, a thioester, respectively);
- $R^1$ and $R^2$ can independently be substituted or non-substituted aliphatic chains with a number of carbon atoms varying from 1 to 20, possibly containing heteroatoms, or groups of the aromatic, arylaliphatic, cycloaliphatic, heterocyclic series, in particular other triazole groups, and they can also contain or be derivatives of bioactive molecules;
- Cyc can be a residue of the cyclo-aliphatic, aromatic or non-aromatic series, saturated or unsaturated, substituted or non-substituted, with a number of C atoms in the cycle ranging from 3 to 8, preferably substituted cyclohexene or substituted cyclohexane; or a residue of the heterocyclic series, aromatic or non-aromatic, saturated or unsaturated, substituted or non-substituted, with a number of C atoms in the cycle ranging from 2 to 7 and a number of heteroatoms in the cycle ranging from 1 to 7, preferably substituted triazole.

The Cyc group can possibly have its own biological activity; the Cyc group must in any case be the product of a cycloaddition reaction belonging to the range of "click chemistry", as defined in the present patent application.

The crosslinked products described above are obtained by means of one or more cycloaddition reactions with the formation of one or more covalent chemical bonds between two or more polysaccharide blocks modified so as to respectively have the chemical structure (see FIG. 4).

For purely illustrative purposes, in FIG. 4, both of the polysaccharide blocks consist of hyaluronate, suitably functionalized at the level of some of its carboxylic groups, but one of the two blocks could also be represented by a different polycarboxylated polysaccharide analogously modified.

In the structures of FIG. 4, the $X^1$, $R^1$ and $Y^1$ groups are thus defined:

- $X^1$ and $X^2$ can independently be O, NH, OC(O), S groups (i.e. the derivative of carboxylic acid can be an ester, an amide, an anhydride, a thioester, respectively);
- $R^1$ and $R^2$ can independently be substituted or non-substituted aliphatic chains with a number of carbon atoms varying from 1 to 20, possibly containing heteroatoms, or groups of the aromatic, arylaliphatic, cycloaliphatic, heterocyclic series, in particular other triazole groups, and they can also contain or be derivatives of bioactive molecules;
- $Y^1$ and $Y^2$ are residues containing groups capable of reacting with each other in a cycloaddition reaction belonging to the range of "click chemistry", as defined according to the present patent application, and preferably residues containing groups capable of reacting with each other in a Diels Alder cycloaddition or a 1,3-dipolar cycloaddition. More specifically, the pair $(Y^1, Y^2)$ is a pair of the (1,3-unsaturated, dienophile), or (1,3-dipole, dipolarophile) type, wherein:
- the 1,3-unsaturated compound is selected from derivatives of 1,3-dienes (also called conjugated dienes), and preferably from 1,3-butadiene, 1-methoxy-3-trimethylsilyloxy-1,3-butadiene, cyclopentadiene, cyclohexadiene, furan;
- the dienophile compound is selected from alkenes, alkynes or derivatives of alkenes or alkynes with one or more electron-attractor groups linked to the double or triple bond, and preferably from acrylates, acrylamides, fumarates, vinylketones, nitro-alkenes, nitro-alkynes, maleic anhydride and quinones;
- the 1,3-dipole compound is selected from derivatives of nitrile-oxides, azides, diazo-alkanes, allenes and nitrones, and preferably from derivatives of azides;
- the dipolarophile compound is selected from alkenes, alkynes or from derivatives of alkenes or alkynes with one or more electron-attractor groups bound to the double or triple bond, and preferably from acrylates, acrylamides, fumarates, vinylketones, nitro-alkenes, nitro-alkynes, maleic anhydride, methylacetylene and quinones.

The polysaccharide derivatives shown in FIG. 4, which can be used as blocks forming the crosslinked products according to the present invention, can be easily prepared starting from hyaluronic acid—or a salt or derivative thereof—or from another polycarboxylated polysaccharide—or a salt or derivative thereof—by means of an esterification, amidation, thioesterification reaction or the formation of an anhydride at the carboxyl level, after activation of the carboxyl itself or, in the case of esterification, of the esterifying alcohol, according to the procedures and expedients already known in the state of the art.

The process for the preparation of the crosslinked derivatives according to the present invention therefore comprises the following two phases:

i) synthesis of partial derivatives (esters, amides, thioesters, anhydrides) of hyaluronic acid and possibly another polycarboxylated polysaccharide or their respective salts or derivatives;

ii) cycloaddition reaction between the synthesized derivatives with the formation of covalent bonds between the chains.

The cycloaddition reactions used in the present invention belong to the so-called "click chemistry" range and consequently have the characteristic of being rapid, simple, efficient and, if the groups involved are suitably selected, also regioselective, in addition to the characteristic of not giving rise to undesired side-products. The ideal conditions of the "click" reactions used in the scope of the present patent application envisage the use of an aqueous solvent, but do not exclude the possibility of alternatively adopting an organic solvent, and preferably an aprotic polar organic solvent, if the species involved in the synthesis (polysaccharide salts or derivatives) are soluble therein, or in a mixed solvent. The concentrations of the single polysaccharide derivatives in the reaction mixture normally range from 1 to 500 mg/ml depending on the type of polysaccharide and the type of derivative, and preferably from 5 to 100 mg/ml. The reaction temperature in both cases normally ranges from 4 to 60° C., in particular from 15 to 40° C., whereas the formation of the crosslinked products and consequently the hydrogels takes place after a stirring time which varies from a few seconds to 30 minutes, in particular from a few seconds to 10 minutes.

The cycloaddition reaction can take place with catalysis on the part of a Cu(I) salt, present in the aqueous reaction mixture at a final concentration ranging from 1 to 50 mg/ml, and preferably from 1 to 5 mg/ml, or with catalysis of a system which generates Cu(I) in situ, and preferably a system consisting of a Cu(II) salt (for example $CuSO_4$) and ascorbic acid in catalytic concentrations, or without any catalyst, if the substituents on the reactive groups described above make the same reaction rapid and efficient also under these conditions.

The hydrogels, object of the present invention and obtained by means of the reaction described above, have the capacity of absorbing further water or solvent and swelling, and one of their characteristics lies in the viscoelastic properties which can be modulated according to the crosslinking degree reached. In particular, these hydrogels can be present in the form of a more or less viscous and mucoadhesive fluid, or in a compact three-dimensional structure of the wall-wall type, and consequently having a greater mechanical resistance (see FIG. 5).

In short, the hydrogels, object of the present invention, can be obtained and modulated considering the following parameters:

i. the molecular weight of the starting polysaccharides or their derivatives;
ii. the derivatization degree of the starting polysaccharides or their derivatives, in relation to the groups subsequently used in the crosslinking formation;
iii. for derivatives of the starting polysaccharides, the type of molecule linked to the carboxylic groups not engaged in the crosslinking and their derivatization degree;
iv. the concentration of the starting materials used for obtaining the gel;
v. the type of $R^1$ groups which act as possible spacers between the polysaccharide and the $Y^1$ groups;
vi. the type of solution in which the gel is prepared.

As the gels thus synthesized derive from a polysaccharide matrix, they are widely applied in the medical field, in particular in the field of viscosupplementation and plastic, oncologic and reconstructive surgery.

The crosslinked derivatives in the form of hydrogels are preferably used in plastic surgery as dermal fillers, in oncologic and reconstructive surgery as fillers in gene therapy as matrices for the release of polynucleotides, in tissue engineering as supports containing cellular material in tissue regeneration.

In particular, in the osteoarticular field, where one of the most widely-used and effective types of treatment for degenerative diseases of the cartilage and synovial tissues is the intra-articular injection of compounds having marked viscoelastic properties, the capacity of modulating the rheological characteristics of the hydrogels described herein by the variation of one or more parameters specified above, has proved to be a powerful instrument for the development of innovative medical devices.

Furthermore, availing of a different approach, the crosslinking method described in the present invention is used for the formation of a hydrogel consisting of hyaluronic acid (and/or a derivative thereof) directly in the synovial cavity, by administering via intra-articular injection, first one component and then the second with or without a catalyst based on Cu(I), with two less painful injections as they consist of solutions which initially have a low viscosity.

Another advantage of the use of the crosslinked derivatives according to the present invention in the osteoarticular field, lies in the fact that crosslinked hyaluronic acid in the form of a hydrogel, especially if derivatized at the carboxyl level by means of a more stable bond such as for example the amide bond, has longer chemical degradation times with respect to those of a viscosupplementing compound injected in fluid form and based on the starting polysaccharide or the polysaccharide crosslinked according to methods different from that object of the present invention, allowing longer residence times in the site of administration.

This latter surprising characteristic can be demonstrated by the results of degradation studies in vitro at 37° C. of a crosslinked derivative of HA (obtained in the form of a hydrogel, as described in example 3 of the present patent application), both in PBS 0.2 M and in artificial plasma.

Observe in the following table, in fact, the comparative data between ACP® 5% (Auto Crosslinked Polymer, internal ester at 5% approximately of HA) and the derivative described as product of example 3, relating to the degradation test in PBS 0.2M at 37° C., where the evaluation parameters of the chemical and rheological stability are the substitution degree of the derivative at the carboxyl level and the dynamic viscosity, respectively. The test was effected by swelling a known quantity of the respective derivatives in a known volume of $H_2O$ and diluting the hydrogel formed with PBS until a concentration of the species of 10 mg/ml is obtained. During incubation at 37° C., the decrease in the substitution degree of the derivatives and the loss of viscosity of the hydrogels obtained were monitored during the various observation times.

| Derivative | Parameter | t = 0 | t = 1 g | T = 2 gg | t = 3 gg | t = 4 gg | t = 5 gg | t = 7 gg | t = 10 gg |
|---|---|---|---|---|---|---|---|---|---|
| ACP ® 5% | Substitution degree (% mol/mol) | 6.9 | 6.7 | 6.3 | 5.9 | 5.8 | 5.4 | 4.5 | 3.2 |
| | Dynamic Viscosity (Pa·s) | 12.5 | 10.4 | 7.1 | 4.6 | 3.1 | 2.0 | 1.2 | 0.7 |
| Crosslinked via click-chemistry | Substitution degree (% mol/mol) | 11.2 | 11.1 | 11.4 | 11.1 | 10.8 | 10.9 | 10.8 | 10.7 |
| | Dynamic Viscosity (Pa·s) | 36.1 | 35.5 | 34.0 | 34.6 | 33.8 | 32.8 | 31.1 | 29.9 |

In addition to an evident chemical stability under physiological conditions, a much longer maintenance of the rheological performance is also observed.

The same versatility, viscoelasticity, biocompatibility and slow biodegradability characteristics therefore allow the crosslinked derivatives according to the present invention to be used as dermal fillers in the field of plastic surgery.

An important characteristic of the hydrogels according to the present invention consists in the fact that a wide range of biologically or pharmacologically active molecules can be incorporated therein during the crosslinking of the polysaccharides without significantly influencing the reaction rate and quantitativity of the yield, and without being involved in the process causing the formation of undesired side-products. The functional groups involved in the cycloaddition reactions used in the process according to the present invention are in fact characterized by a highly specific reactivity or they can in any case be selected so that the functions present in the molecule to be incorporated are inert in their respect.

An object of the present invention therefore relates to a method for the preparation of controlled release systems of pharmacologically active molecules, in the form of gels, obtained with the process previously described, charged with one or more biologically or pharmacologically active molecules, wherein these molecules are dissolved in the reaction solvent (whether this be aqueous or organic) before the formation of the gel together with the partial polysaccharide derivatives to be crosslinked, and then remain physically and homogeneously incorporated in the polymeric matrix formed following the crosslinking.

In the controlled release systems of biologically and/or pharmacologically active molecules and/or macromolecules according to the present invention, the molecules and/or macromolecules having a biological or pharmacological activity are selected from active principles such as proteins, growth factors, enzymes, antitumoral drugs, cytostatics, steroid and non-steroid anti-inflammatory drugs, antibiotics, antimicrobial drugs, antiviral drugs, antifungal drugs, anesthetics, analgesics, narcotics, cholinergic and adrenergic agonists and antagonists, antithrombotic drugs, anticoagulants, haemostatic drugs, fibrinolytic and thrombolytic drugs for topic, subcutaneous, intramuscular or intra-articular use.

The release curves of an antineoplastic drug (doxorubicin) and an anti-inflammatory drug (benzydamine) incorporated in matrices in the form of hydrogels obtained after crosslinking via the Huisgen reaction of suitable azide and alkyne derivatives of hyaluronic acid are shown hereunder for illustrative purposes (for further and more detailed descriptions see also the section relating to the examples, in particular example 13).

In the first case it is observed that the maximum quantity of doxorubicin hydrochloride is released in about 50 h and is equal to 50% of the quantity initially incorporated in the gel (see FIG. 6).

In the second diagram the maximum quantity of benzydamine hydrochloride is released in about 6 h and is equal to 80% of the quantity of drug initially incorporated in the gel (see FIG. 7).

These controlled release systems of drugs in the form of gels can have numerous fields of application, but in particular in the dermatological, oncologic, pneumological and osteo-articular fields.

In particular, in the case of intra-articular use, the above gel can contain active principles such as anti-inflammatory substances, metal-protease inhibitors, NO synthase inhibitors, or other biologically active molecules for the treatment of arthrosic and/or arthritic pathologies, thus obtaining a slow release of the active principle(s), associated with the mainly mechanical viscosupplementation action offered by the gel.

In particular, an object of the present invention relates to the use of controlled release systems in oncologic reconstructive surgery or in oncologic neurosurgery, following the removal of cancer masses, wherein the hydrogel contains antineoplastic and/or cytostatic drugs and/or their precursors as pharmacologically active molecules.

On the basis of the specific advantages provided by the good biocompatibility, slow biodegradation and significant mucoadhesion, the loco-regional administration of these controlled release systems, charged with antineoplastic and/or cytostatic drugs proves to be particularly effective and advantageous, in the case for example of facial surgery.

In these forms of application, in fact, the function of "filler" of the crosslinked polysaccharide matrix itself, is associated with the activity of the drug which is slowly released by said matrix, in order to prevent the formation of relapsing neoplasm.

The possible administration sites of the previously described controlled release systems comprise all those tissue cavities or spaces deriving from surgical interventions for the removal of tumoral masses, where it is appropriate to introduce a biocompatible product in the form of a medicated hydrogel having both a structural and filling function and a pharmacological activity. In particular, intrathecal administrations are of particular interest, following the removal of cerebral neoplasm (for example glyoblastoms), intraperitoneal administrations following the removal of colic, vesical, hepatic and pancreatic tumors, and in the case of reconstructive mastoplastics administrations after the removal of breast tumors.

Examples of pharmacologically active molecules which can be used in this form of application of the controlled release systems according to the present invention are all those having a known antitumoral or cytostatic activity and/or possible precursors thereof, in particular molecules pharmacologically effective in the treatment of the neoplasm listed above, and preferably paclitaxel, doxorubicin, irinothecan, 5-fluorouracil, gemcitabin, vincristine and methotrexate.

The following examples are provided for a better illustration of the present invention.

EXAMPLE 1

Amidation of HANa with 11-azide-3,6,9-trioxaundecane-1-amine in an Aqueous Solvent at pH=4 in the Presence of EDC.HCl and NHS 2 g of 700 kDa HA sodium salt were dissolved in 80 ml of 100 mM MES buffer, pH=4. The following reactants were then added in sequence: 1.43 g of EDC.HCl (N-(3,dimethylaminopropyl)-N'-ethylcarbodiimide hydrochloride) and 0.86 g of NHS (N-hydroxysuccinimide), and subsequently 3.30 ml of 11-azide-3,6,9-trioxaundecane-1-amine at 90%. The mixture was left under stirring at room temperature for 24 hours, it was then dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried. Product 1 (see FIG. 8) was recovered as a white powder.

Reaction of Product 1 with Propargylamine 500 mg of product 1 were dissolved in 20 ml of distilled water. 2 ml of propargylamine and 2 ml of a 2% w/v aqueous solution of CuCl prepared previously were then added. The mixture was stirred for 1 hour at room temperature, the solution was dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried recovering the product as a white powder (see FIG. 9).

EXAMPLE 2

Amidation of HANa with Propargylamine in an Aqueous Solvent at pH=4 in the Presence of EDC.HCl and NHSS 1.43 g of EDC.HCl, 1.62 g of NHSS and then 1.04 ml of propargylamine were added to 2 g of 200 kDa HA sodium salt dissolved in 80 ml of 100 mM MES buffer, pH=4. The mixture was left under stirring at room temperature for 24 hours, it was then transferred to dialysis tubes (MWCO=12 kDa) and dialyzed against a saturated solution of NaCl for 24 hours, and then against distilled water until a constant conductivity was reached. The solution was subsequently frozen in liquid nitrogen and freeze-dried for the recovery of product 2 (see FIG. 10) as a white powder.

Reaction of Product 2 with 11-azide-3,6,9-trioxaundecane-1-amine 500 mg of product 2 were dissolved in 20 ml of distilled water. 3 ml of 11-azide-3,6,9-trioxaundecane-1-amine and 2 ml of a 2% w/v aqueous solution of CuCl prepared previously were then added. The mixture was stirred for 1 hour at room temperature, the solution was dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried recovering the product as a white powder (see FIG. 11).

EXAMPLE 3

Amidation of HANa with 11-azide-3,6,9-trioxaundecane-1-amine in an Aqueous Solvent at pH=4 in the Presence of EDC.HCl and NHS 2 g of 69 kDa HA sodium salt were dissolved in 80 ml of 100 mM MES buffer, pH=4. 1.43 g of EDC.HCl (N-(3,dimethylaminopropyl)-N'-ethylcarbodiimide hydrochloride) and 0.86 g of NHS (N-hydroxysuccinimide), and subsequently 3.30 ml of 11-azide-3,6,9-trioxaundecane-1-amine at 90%, were then added in sequence. The mixture was left under stirring at room temperature for 24 hours, it was then dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried, recovering product 3 (having the same chemical structure as FIG. 8) as a white powder.

Amidation of HANa with Propargylamine in an Aqueous Solvent at pH=4 in the Presence of EDC.HCl and NHS 1.43 g of EDC.HCl, 0.86 g of NHS and then 1.04 ml of propargylamine were added to 2 g of 69 kDa HA sodium salt dissolved in 80 ml of 100 mM MES buffer, pH=4. The reaction was left under stirring at room temperature for 24 hours, it was then transferred to dialysis tubes 12 kDa and dialyzed against a saturated solution of NaCl for 24 hours, and then against distilled water until a constant conductivity was reached. The solution was subsequently frozen in liquid nitrogen and freeze-dried for the recovery of product 4 (having the same chemical structure as FIG. 10) as a white powder.

Formation of the Hydrogel of Hyaluronic Acid in an Aqueous Solvent 400 mg of product 3 and 400 g of product 4 were dissolved separately in 8 ml of distilled water until complete dissolution. 30 mg of CuCl were dissolved apart in 1.50 ml of distilled water. The solutions of the polymers were then mixed, subsequently adding the solution of CuCl and vortically stirring for a few minutes until the formation of the gel (see FIG. 12). The gel was then dialyzed against distilled water to remove the excess CuCl until a constant weight of the gel.

EXAMPLE 4

Amidation of HANa with 11-azide-3,6,9-trioxaundecane-1-amine in an Aqueous Solvent at pH=6 in the Presence of EDC.HCl and NHSS 1 g of 200 kDa HA sodium salt was dissolved in 80 ml of 100 mM MES buffer, pH=6. 478 mg of EDC.HCl and 540 mg of NHSS (N-hydroxysulfosuccinimide), and subsequently 1.65 ml of 11-azide-3,6,9-trioxaundecane-1-amine at 90%, were then added. The solution was stirred at room temperature for 8 hours, and then dialyzed in 12 kDa cut-off tubes against a saturated solution of NaCl, and then against distilled water until a constant conductivity was reached. The solution was subsequently transferred to a flask, frozen in liquid nitrogen and freeze-dried. Product 5 (having the same chemical structure as FIG. 8) was recovered as a white powder.

Amidation of HANa with Propargylamine in an Aqueous Solvent at pH=6 in the Presence of EDC.HCl and NHSS 1 g of 200 kDa HA sodium salt was dissolved in 80 ml of 100 mM MES buffer, pH=6. 478 mg of EDC.HCl and 540 mg of NHSS, followed by 0.520 ml of propargylamine were then added. The system was left under stirring at room temperature for 8 hours, it was then dialyzed (MWCO=12 kDa) against a saturated solution of NaCl for 24 hours, and then against distilled water until a constant conductivity was reached. The solution transferred to a flask was subsequently frozen and freeze-dried for the recovery of product 2 as a white powder.

Formation of the Hydrogel of Hyaluronic Acid in an Aqueous Solvent in the Presence of BSA 20 ml of a 1% w/v aqueous solution of bovine serum albumin (BSA) were prepared; 300 mg of product 5 were then completely dissolved in 6 ml of the above solution and an analogous procedure was then followed for product 2. A 2% w/v aqueous solution of CuCl was prepared apart. The solutions of the polymers were mixed, subsequently adding 1 ml of a CuCl solution and stirring vortically for a few minutes until the formation of the gel of FIG. 12. The gel was then dialyzed against distilled water until a constant weight was reached.

EXAMPLE 5

Amidation of HANa with
11-azide-3,6,9-trioxaundecane-1-amine in an
Aqueous Solvent at pH=4 in the Presence of
EDC.HCl and NHS 2 g of 69 kDa HA sodium salt were dissolved in 80 ml of 100 mM MES buffer, pH=4. 1.43 g of EDC.HCl (N-(3,dimethylaminopropyl)-N'-ethylcarbodiimide hydrochloride), 0.86 g of NHS (N-hydroxysuccinimide) and subsequently 3.30 ml of 11-azide-3,6,9-trioxaundecane-1-amine at 90%, were then added in sequence. The reaction was left under stirring at room temperature for 24 hours, and then dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried, recovering product 3 (having the same chemical structure as FIG. 8) as a white powder.

Amidation of HANa with Propargylamine in an
Aqueous Solvent at pH=4 in the Presence of
EDC.HCl and NHS 1.43 g of EDC.HCl, 0.86 g of NHS and then 1.04 ml of propargylamine were added to 2 g of 69 kDa HA sodium salt dissolved in 80 ml of 100 mM MES buffer, pH=4. The reaction was left under stirring at room temperature for 24 hours, the solution was then transferred to 12 kDa cut-off dialysis tubes and dialyzed against a saturated solution of NaCl for 24 hours, and then against distilled water until a constant conductivity was reached. The solution was subsequently frozen in liquid nitrogen and freeze-dried for the recovery of product 4 (having the same chemical structure as FIG. 10) as a white powder.

Formation of the Hydrogel of Hyaluronic Acid in an
Aqueous Solvent in the Presence of BSA 25 ml of a 2% w/v aqueous solution of bovine serum albumin (BSA) were prepared; 400 mg of product 3 and 400 mg of product 4 were then completely dissolved in 8 ml of the above solution. 30 mg of CuCl were dissolved apart in 1.50 ml of distilled water. The solutions of the polymers were then mixed, subsequently adding the solution of CuCl and stirring vortically for a few minutes until the formation of the gel of FIG. 12. The gel was then dialyzed against distilled water to remove the excess CuCl.

EXAMPLE 6

Amidation of HANa with
11-azide-3,6,9-trioxaundecane-1-amine in an
Aqueous Solvent at pH=4 in the Presence of
EDC.HCl and NHS 2 g of 69 kDa HA sodium salt were dissolved in 80 ml of 100 mM MES buffer, pH=4. 1.43 g of EDC.HCl (N-(3,dimethylaminopropyl)-N'-ethylcarbodiimide hydrochloride), 0.86 mg of NHS (N-hydroxysuccinimide) and subsequently 3.30 ml of 11-azide-3,6,9-trioxaundecane-1-amine at 90%, were then added in sequence. The reaction was left under stirring at room temperature for 24 hours, and then dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried, recovering product 3 (having the same chemical structure as FIG. 8) as a white powder.

Amidation of HANa with Propargylamine in an
Aqueous Solvent at pH=4 in the Presence of
EDC.HCl and NHS 1.43 g of EDC.HCl, 0.86 g of NHS and then 1.04 ml of propargylamine were added to 2 g of 69 kDa HA sodium salt dissolved in 80 ml of 100 mM MES buffer, pH=4. The reaction was left under stirring at room temperature for 24 hours, the solution was then transferred to 12 kDa cut-off dialysis tubes against a saturated solution of NaCl for 24 hours, and then against distilled water until a constant conductivity was reached. The solution was subsequently frozen in liquid nitrogen and freeze-dried for the recovery of product 4 (having the same chemical structure as FIG. 10) as a white powder.

Formation of the Hydrogel of Hyaluronic Acid in an
Aqueous Solvent in the Presence of IL-2

400 mg of product 3 and 400 mg of product 4 were dissolved separately in 8 ml of distilled water until complete dissolution. 0.5 mg of interleukin 2 (IL 2) were also dissolved in 0.5 ml of water. 30 mg of CuCl were dissolved apart in 1.50 ml of distilled water. The solutions of the polymers were then mixed, the solution of interleukin 2 was subsequently added and the mixture was left under light stirring. The solution of CuCl was finally added, stirring vortically for a few minutes until the formation of the gel (see FIG. 12). The gel was then dialyzed against distilled water to remove the excess CuCl.

Formation of the Hydrogel of Hyaluronic Acid in an
Aqueous Solvent in the Presence of Doxorubicin
Hydrochloride 400 mg of product 3 and 400 mg of product 4 were dissolved separately in 8 ml of distilled water until complete dissolution. 15 mg of doxorubicin hydrochloride were also dissolved in 1 ml of water. 30 mg of CuCl were dissolved apart in 1.50 ml of distilled water. The solutions of the polymers were then mixed, the solution of doxorubicin hydrochloride was subsequently added and the mixture was left under light stirring. The solution of CuCl was finally added, stirring vortically for a few minutes until the formation of the gel (see FIG. 12). The gel was then dialyzed against distilled water to remove the excess CuCl.

EXAMPLE 7

Amidation of CMC with
11-azide-3,6,9-trioxaundecane-1-amine in an
Aqueous Solvent at pH=4 in the Presence of
EDC.HCl and NHS 2 g of CMC (carboxymethylcellulose) were dissolved in 80 ml of 100 mM MES buffer, pH=4. 1.57 g of EDC.HCl, 0.94 g of NHS, and subsequently 2.71 ml of 11-azide-3,6,9-trioxaundecane-1-amine at 90%, were added. The solution was left under stirring at room temperature for 24 hours, and then dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried, recovering product 6 as a white powder.

Amidation of HANa with Propargylamine in an Aqueous Solvent at pH=4 in the Presence of EDC.HCl and NHS 2.87 g of EDC.HCl, 1.72 g of NHS and then 1.73 ml of propargylamine were added to 2 g of 69 kDa HA sodium salt dissolved in 80 ml of 100 mM MES buffer, pH=4. The reaction was left under stirring at room temperature for 24 hours, the solution was then transferred to dialysis tubes (MWCO=12 kDa) and dialyzed against a saturated solution of NaCl for 24 hours, and then against distilled water until a constant conductivity was reached. The solution was subsequently frozen in liquid nitrogen and freeze-dried, recovering product 4 (see FIG. 10) as a white powder.

Formation of the Mixed Hydrogel of Hyaluronic Acid and Carboxymethylcellulose in an Aqueous Solvent 500 mg of product 6 (derivative of CMC) were dissolved in 10 ml of distilled water, and analogously for product 4. An aqueous solution of 2% w/v CuCl was prepared apart. The solutions of the two different polymers were mixed and 1.50 ml of the solution of CuCl was then added, stirring vortically for a few minutes until the formation of the gel (FIG. 13). The gel was then dialyzed against distilled water until a constant weight was reached.

EXAMPLE 8

Amidation of HANa with 11-azide-3,6,9-trioxaundecane-1-amine in an Aqueous Solvent at pH=4 in the Presence of EDC.HCl and NHS 2 g of 200 kDa HA sodium salt were dissolved in 80 ml of 100 mM MES buffer, pH=4. 1.43 g of EDC.HCl (N-(3,dimethylaminopropyl)-N'-ethylcarbodiimide hydrochloride), 0.86 g of NHS (N-hydroxysuccinimide) and subsequently 5.50 ml of 11-azide-3,6,9-trioxaundecane-1-amine at 90%, were then added in sequence. The reaction was left under stirring at room temperature for 24 hours, and then put on dialysis against a saturated solution of NaCl for 24 hours, and then against distilled water until a constant conductivity was reached. The solution was subsequently transferred to a flask, frozen in liquid nitrogen and freeze-dried, recovering product 5 (having the same chemical structure as FIG. 8) as a white powder.

Amidation of CMC with Propargylamine in an Aqueous Solvent at pH=4 in the Presence of EDC.HCl and NHS 2.36 g of EDC.HCl, 1.41 g of NHS and then 5.42 ml of propargylamine were added to 2 g of CMC dissolved in 80 ml of 100 mM MES buffer, pH=4. The reaction was left under stirring at room temperature for 24 hours, the solution was then transferred to dialysis tubes (MWCO=12 kDa) and dialyzed against a saturated solution of NaCl for 24 hours, and then against distilled water until a constant conductivity was reached. The solution was subsequently frozen in liquid nitrogen and freeze-dried, recovering product 7 as a white powder.

Formation of the Mixed Hydrogel of Hyaluronic Acid and CMC in an Aqueous/Organic Solvent 500 mg of product 5 and 500 mg of product 7 (derivative of CMC) were dissolved separately in 5 ml of distilled water and 5 ml of NMP. 30 mg of CuCl were dissolved apart in 1.50 ml of distilled water. The solutions of the polymers were then mixed, the solution of CuCl was then added, stirring vortically for a few minutes until the formation of the mixed hyaluronic acid/carboxymethylcellulose gel. The gel was then dialyzed towards distilled water to remove the CuCl and organic solvent, said dialysis being carried out until a constant weight of the gel was reached.

EXAMPLE 9

Amidation of Hyaffllp50 with 11-azide-3,6,9-trioxaundecane-1-amine in an aqueous solvent at pH=4 in the Presence of EDC.HCl and NHS 2 g of Hyaffllp50 were dissolved in 80 ml of 100 mM MES buffer, pH=4. 1.32 g of EDC.HCl (N-(3,dimethylaminopropyl)-N'-ethylcarbodiimide hydrochloride), 0.79 g of NHS (N-hydroxysuccinimide) and subsequently 3.04 ml of 11-azide-3,6,9-trioxaundecane-1-amine at 90%, were then added in sequence. The mixture was left under stirring at room temperature for 24 hours, and then dialyzed (MWCO=12 kDa) against a saturated solution of NaCl for 24 hours, and then against distilled water until a constant conductivity was reached. The solution was subsequently transferred to a flask, frozen in liquid nitrogen and freeze-dried, recovering product 8 as a white powder.

Amidation of Hyaffllp50 with Propargylamine in an Aqueous Solvent at pH=4 in the Presence of EDC.HCl and NHS 1.32 g of EDC.HCl, 0.79 g of NHS and then 0.95 ml of propargylamine were added to 2 g of Hyaffllp50 dissolved in 80 ml of 100 mM MES buffer, pH=4. The reaction was left under stirring at room temperature for 24 hours, the solution was then transferred to dialysis tubes (MWCO=12 kDa) and dialyzed against a saturated solution of NaCl for 24 hours, and then against distilled water until a constant conductivity was reached. The solution was subsequently frozen in liquid nitrogen and freeze-dried, recovering product 9 as a white powder.

Formation of the Hydrogel of Hyaffllp50 in an Aqueous/Organic Solvent 400 mg of each of the two derivatives 8 and 9 described above were dissolved separately in 4 ml of distilled water and 4 ml of NMP. 30 mg of CuCl were dissolved apart in 1.50 ml of distilled water. The solutions of the polymers were then mixed, the solution of CuCl was then added and the mixture stirred vortically for a few minutes until the formation of the gel (see FIG. 14). The gel was then dialyzed against distilled water to remove the excess CuCl until a constant weight of the gel was reached.

EXAMPLE 10

Amidation of Hyaff9p10 with 11-azide-3,6,9-trioxaundecane-1-amine in an aqueous solvent at pH=6 in the Presence of EDC.HCl and NHSS 1 g of Hyaff9p10 was dissolved in 80 ml of 100 mM MES buffer, pH=6. 470 mg of EDC.HCl, 530 mg of NHSS (N-hydroxysulfosuccinimide) and subsequently 1.60 ml of 11-azide-3,6,9-trioxaundecane-1-amine at 90%, were then added. The solution was left under stirring at room temperature for 8 hours, and then dialyzed in tubes (cut-off 12 kDa) against a saturated solution of NaCl, and then against distilled water until a constant conductivity was reached. The solution was subsequently transferred to a flask, frozen in liquid nitrogen and freeze-dried. Product 10 was recovered as a white powder.

Amidation of Hyaff9p10 with Propargylamine in an Aqueous Solvent at pH=6 in the Presence of EDC.HCl and NHSS 1 g of Hyaff9p10 was dissolved in 80 ml of MES buffer 100 mM, pH=6. 470 mg of EDC.HCl, 540 mg of NHSS and then 530 ml (3×) of propargylamine were then added to the solution. The system was left under stirring at room temperature for 8 hours and dialyzed (MWCO=12 kDa) against a saturated solution of NaCl for 24 hours, and then against distilled water until a constant conductivity was reached. The solution was transferred to a flask and subsequently frozen and freeze-dried for the recovery of product 11 as a white powder.

Formation of the Hydrogel of Hyaff9p10 in an Aqueous Solvent 300 mg of product 10 and 300 mg of product 11 were dissolved completely and separately in 6 ml of distilled water. A 2% w/v aqueous solution of CuCl was prepared apart. The solutions of the polymers were then mixed, adding 1 ml of the solution of CuCl and the mixture was stirred vortically for a few minutes until the formation of the gel (see FIG. 15). The gel was then dialyzed against distilled water until a constant weight of the gel was reached.

EXAMPLE 11

Amidation of HANa with 11-azide-3,6,9-trioxaundecane-1-amine in an Aqueous Solvent at pH=4 in the Presence of EDC.HCl and NHS 2 g of 200 kDa HA sodium salt are dissolved in 80 ml of 50 mM MES buffer, pH=4. 2.90 g of EDC.HCl (N-(3, dimethylaminopropyl)-N'-ethylcarbodiimide hydrochloride), 1.77 g of NHS (N-hydroxysuccinimide), and 5.50 ml of 11-azide-3,6,9-trioxaundecane-1-amine at 90%, are then added in sequence. The reaction is left under stirring at room temperature for 48 h and is then dialyzed (MWCO=14 kDa) against a saturated solution of NaCl for 24 h, and against distilled water until a constant conductivity has been reached. The solution is subsequently transferred to a flask, frozen in liquid nitrogen and then freeze-dried. Product 1 is recovered (see FIG. 16) as a white powder.

Amidation of HANa with Propargylamine in an Aqueous Solvent at pH=4 in the Presence of EDC.HCl and NHS 2.90 g of EDC.HCl, 1.77 g of NHS and then 1.73 ml of propargylamine are added to 2 g of 200 kDa HA sodium salt dissolved in 80 ml of 50 mM MES buffer, pH=4. The reaction is left for 48 h under stirring at room temperature, the solution is then transferred to dialysis tubes (MWCO=14 kDa) and dialyzed against a saturated solution of NaCl for 24 h, and then against distilled water until a constant conductivity has been reached. The solution is subsequently frozen in liquid nitrogen and freeze-dried for the recovery of product 2 (see FIG. 17) as a white powder.

Formation of the Hydrogel of Hyaluronic Acid with Catalytic $CuSO_4.5H_2O$ and Ascorbic Acid in an Aqueous Solvent in the Present of BSA 25 ml of a 2% w/v aqueous solution of bovine serum albumin (BSA) are prepared; 500 mg of product 1 and 500 mg of product 2 are then dissolved in 14 ml of the above solution. 2 ml of an aqueous solution obtained with 50 mg of $CuSO_4.5H_2O$ and 4 ml of an aqueous solution of 40 mg of ascorbic acid are subsequently added, stirring vortically for a few minutes. The rapidly formed gel (see FIG. 18) incorporates the BSA protein.

Formation of the Hydrogel of Hyaluronic Acid Crosslinked with Catalytic CuCl in an Aqueous Solvent in the Presence of Doxorubicin Hydrochloride 29 mg of doxorubicin hydrochloride are dissolved in 2 ml of water and 50 mg of product 1 and 50 mg of product 2 synthesized as described above, are then added. 830 μL of a 1% w/V solution of CuCl are subsequently added to the solution and the gel is formed after a few minutes directly incorporating the drug present in solution.

Release Measurements of the Drug Doxorubicin Hydrochloride from Hydrogels Based on Crosslinked Hyaluronic Acid Obtained with Catalytic CuCl The quantity of doxorubicin hydrochloride released from the hydrogel in 100 ml of distilled water, is determined by U.V. spectrophotometric measurements at $\lambda=486$ nm by interpolation of the absorbance values on a calibration line constructed using solutions of the drug at known concentration.

The release measurements of the drug are performed on the hydrogel described above.

The maximum quantity of doxorubicin hydrochloride is released over a period of about 160 h and is equal to 25% of the quantity of drug initially incorporated in the gel (see FIG. 19).

Formation of the Hydrogel of Hyaluronic Acid Crosslinked with Catalytic CuCl in an Aqueous Solvent in the Presence of Benzydamine Hydrochloride 69 mg of benzydamine hydrochloride are dissolved in 2 ml of water and 50 mg of product 1 and 50 mg of product 2 synthesized as described above, are then added.

830 μL of a 1% w/V solution of CuCl are subsequently added to the solution and the gel is formed after a few minutes directly incorporating the drug.

Release Measurements of the Drug Benzydamine Hydrochloride from Hydrogels Based on Crosslinked Hyaluronic Acid Obtained with Catalytic CuCl The quantity of benzydamine hydrochloride released from the hydrogel, in 100 ml of a phosphate buffer solution pH=7.4, is determined by means of U.V. spectrophotometric measurements at λ=308 nm by interpolation of the absorbance values on a calibration line constructed using solutions of the drug at a known concentration.

The release measurements of the drug are performed on the hydrogel described above.

The maximum quantity of benzydamine hydrochloride is released over a period of about 3.5 h and is equal to 88% of the quantity of drug initially incorporated in the gel (see FIG. 20).

Formation of the Hydrogel of Hyaluronic Acid Crosslinked with Catalytic $CuSO_4.5H_2O$ and Ascorbic Acid in an Aqueous Solvent in the Presence of Benzydamine Hydrochloride 50 mg of product 1 and 50 mg of product 2 are dissolved in 1.3 ml of distilled water and separately 13.8 mg of benzydamine hydrochloride are dissolved in 0.5 ml of distilled water. The solution of hyaluronic acid is mixed with that of benzydamine hydrochloride; 0.1 ml of an aqueous solution obtained with 50 mg of $CuSO_4.5H_2O$ in 1 ml of $H_2O$ and 0.1 ml of an aqueous solution of 20 mg of ascorbic acid are then added.

The mixture is stirred vortically for a few minutes. The rapidly formed gel incorporates the benzydamine hydrochloride inside.

Release Measurements of the Drug Benzydamine Hydrochloride from Hydrogels Based on Crosslinked Hyaluronic Acid Obtained with Catalytic $CuSO_4.5H_2O$ The quantity of benzydamine hydrochloride released from the hydrogel, in 100 ml of distilled water, is determined by means of U.V. spectrophotometric measurements at λ=308 nm by interpolation of the absorbance values on a calibration line constructed using solutions of the drug at known concentration.

The release measurements of the drug are performed on the hydrogel described above.

The maximum quantity of benzydamine hydrochloride is released over a period of about 5 h and is equal to 70% of the quantity of drug initially incorporated in the gel (see FIG. 21).

EXAMPLE 12

Amidation of HANa with 11-azide-3,6,9-trioxaundecane-1-amine in an Aqueous Solvent at pH=4 in the Presence of EDC.HCl and NHS 2 g of 200 kDa HA sodium salt are dissolved in 80 mL of 50 mM MES buffer, pH=4. 2.90 g of EDC.HCl (N-(3, dimethylaminopropyl)-N'-ethylcarbodiimide hydrochloride), 1.77 g of NHS (N-hydroxysuccinimide), and 5.50 ml of 11-azide-3,6,9-trioxaundecane-1-amine at 90%, are subsequently added in sequence. The reaction is left under stirring at room temperature for 48 h, and is then (MWCO=14 kDa) dialyzed against a saturated solution of NaCl for 24 h, and against distilled water until a constant conductivity has been reached. The solution is then transferred to a flask, frozen in liquid nitrogen and then freeze-dried. Product 1 is recovered as a white powder.

Reaction of Product 1 with 1,4-Diethynylbenzene in an Aqueous/Organic Solvent with Catalytic $CuSO_4.5H_2O$ and Ascorbic Acid 500 mg of product 1 are dissolved in 45 ml of distilled water and 150 mg of 1,4-diethynylbenzene are dissolved in 1.5 ml of DMSO. The solutions are mixed, 1.5 ml of an aqueous solution obtained with 50 mg of $CuSO_4.5H_2O$ in 3 ml of $H_2O$ and 2 ml of an aqueous solution of 88 mg of ascorbic acid are then added. The mixture is stirred for 4 h at room temperature, the solution is then (MWCO=14 kDa) dialyzed against a saturated solution of EDTA for 24 h, and then against distilled water until a constant conductivity has been reached. The solution is subsequently transferred to a flask, frozen in liquid nitrogen and freeze-dried, recovering the product (see FIG. 22) as a white powder.

Reaction of Product 1 with 1,6-Heptadiyne in an Aqueous/Organic Solvent with Catalytic $CuSO_4.5H_2O$ and Ascorbic Acid 500 mg of product 1 are dissolved in 45 ml of distilled water and 0.13 ml of 1,6-Heptadiyne are dissolved in 1.5 ml of DMSO. The solutions are mixed, 1.5 ml of an aqueous solution obtained with 50 mg of $CuSO_4.5H_2O$ in 3 ml of $H_2O$ and 2 ml of an aqueous solution of 88 mg of ascorbic acid are then added. The mixture is stirred for 4 h at room temperature, the solution is then (MWCO=14 kDa) dialyzed against a saturated solution of EDTA for 24 h, and then against distilled water until a constant conductivity has been reached. The solution is subsequently transferred to a flask, frozen in liquid nitrogen and freeze-dried, recovering the product (see FIG. 23) as a white powder.

Reaction of Product 1 with 1,8-Nonadiyne in an Aqueous/Organic Solvent with Catalytic $CuSO_4.5H_2O$ and Ascorbic Acid 500 mg of product 1 are dissolved in 45 ml of distilled water and 0.18 ml of 1,8-Nonadiyne are dissolved in 1.5 ml of DMSO. The solutions are mixed, 1.5 ml of an aqueous solution obtained with 50 mg of $CuSO_4.5H_2O$ in 3 ml of $H_2O$ and 2 ml of an aqueous solution of 88 mg of ascorbic acid are subsequently added. The mixture is stirred for 4 h at room temperature, the solution is then (MWCO=14 kDa) dialyzed against a saturated solution of EDTA for 24 h, and then towards distilled water until a constant conductivity has been reached. The solution is then transferred to a flask, frozen in liquid nitrogen and freeze-dried, recovering the product (see FIG. 24) as a white powder.

Reaction of Product 1 with Propargyl Ether in an Aqueous/Organic Solvent with Catalytic $CuSO_4.5H_2O$ and Ascorbic Acid 500 mg of product 1 are dissolved in 45 ml of distilled water and 0.12 ml of propargyl ether are dissolved in 1.5 ml of DMSO. The solutions are mixed, 1.5 ml of an aqueous solution obtained with 50 mg of $CuSO_4.5H_2O$ in 3 ml of $H_2O$ and 2 ml of an aqueous solution of 88 mg of ascorbic acid are subsequently added. The mixture is stirred for 4 h at room temperature, the solution is then dialyzed (MWCO=14 kDa) against a saturated solution of EDTA for 24 h, and then against distilled water until a constant conductivity has been reached. The solution is then transferred to a flask, frozen in liquid nitrogen and freeze-dried, recovering the product (see FIG. 25) as a white powder.

EXAMPLE 13

Amidation of HANa with 11-azide-3,6,9-trioxaundecane-1-amine in an Aqueous Solvent at pH=4 in the Presence of EDC.HCl and NHS 2 g of 200 kDa HA sodium salt are dissolved in 80 ml of 50 mM MES buffer, pH=4. 2.90 g of EDC.HCl (N-(3, dimethylaminopropyl)-N'-ethylcarbodiimide hydrochloride), 1.77 g of NHS (N-hydroxysuccinimide), and then 5.50 ml of 11-azide-3,6,9-trioxaundecane-1-amine at 90%, are subsequently added in sequence. The reaction is left under stirring at room temperature for 48 h, and is then dialyzed (MWCO=14 kDa) against a saturated solution of NaCl for 24 h, and against distilled water until a constant conductivity has been reached. The solution is then transferred to a flask, frozen in liquid nitrogen and then freeze-dried. Product 1 is recovered as a white powder.

Formation of the Hydrogel of Hyaluronic Acid with 1,4-Diethynylbenzene Obtained with Catalytic $CuSO_4.5H_2O$ and Ascorbic Acid in an Aqueous/Organic Solvent in the Presence of Doxorubicin Hydrochloride 100 mg of product 1 are dissolved in 1.1 ml of distilled water and 3 mg of 1,4-Diethynylbenzene are dissolved separately in 0.2 ml of DMSO, whereas 23.2 mg of doxorubicin hydrochloride are dissolved in 0.5 ml of distilled water. The three solutions are mixed, 0.1 ml of an aqueous solution obtained with 50 mg of $CuSO_4.5H_2O$ in 1 ml of $H_2O$ and 0.1 ml of an aqueous solution of 20 mg of ascorbic acid are then added. The mixture is stirred vortically for a few minutes. The rapidly formed gel (see FIG. 26) incorporates the doxorubicin hydrochloride inside.

Release Measurements of the Drug Doxorubicin Hydrochloride from a Hydrogel Based on Hyaluronic Acid with 1,4-diethynylbenzene Obtained with Catalytic $CuSO_4.5H_2O$ and Ascorbic Acid in an Aqueous/Organic Solvent, Crosslinked According to the Structure Indicated Above The quantity of doxorubicin hydrochloride released from the hydrogel, in 100 ml of distilled water, is determined by means of U.V. spectrophotometric measurements at $\lambda=486$ nm by interpolation of the absorbance values on a calibration line constructed using solutions of the drug at known concentration.

The release measurements of the drug are effected on the hydrogel described above.

The maximum quantity of doxorubicin hydrochloride is released over a period of about 50 h and is equal to 50% of the quantity of drug initially incorporated in the gel (see FIG. 27).

Formation of the Hydrogel of Hyaluronic Acid with 1,6-Heptadiyne Obtained with Catalytic $CuSO_4.5H_2O$ and Ascorbic Acid in an Aqueous/Organic Solvent in the Presence of Doxorubicin Hydrochloride 100 mg of product 1 are dissolved in 1.1 ml of distilled water; a solution of 140 µl of 1,6-Heptadiyne in 9.86 ml of DMSO are prepared separately, whereas 23.2 mg of doxorubicin hydrochloride are dissolved in 0.5 ml of distilled water. The solution of hyaluronic acid is mixed with that of doxorubicin and with 0.2 ml of that of 1,6-Heptadiyne; 0.1 ml of an aqueous solution obtained with 50 mg of $CuSO_4.5H_2O$ in 1 ml of $H_2O$ and 0.1 ml of an aqueous solution of 20 mg of ascorbic acid are then added. The mixture is stirred vortically for a few minutes. The rapidly formed gel (see FIG. 28) incorporates the doxorubicin hydrochloride inside.

Release Measurements of the Drug Doxorubicin Hydrochloride from a Hydrogel Based on Hyaluronic Acid with 1,6-heptadiyne Obtained with Catalytic $CuSO_4.5H_2O$ and Ascorbic Acid The quantity of doxorubicin hydrochloride released from the hydrogel, in 100 ml of distilled water, is determined by means of U.V. spectrophotometric measurements at $\lambda=486$ nm by interpolation of the absorbance values on a calibration line constructed using solutions of the drug at known concentration.

The maximum quantity of doxorubicin hydrochloride is released over a period of about 250 h and is equal to 23% of the quantity of drug initially incorporated in the gel (see FIG. 29).

Formation of the Hydrogel of Hyaluronic Acid with 1,6-Heptadiyne Obtained with Catalytic $CuSO_4.5H_2O$ in an Aqueous/Organic Solvent in the Presence of Benzydamine Hydrochloride 100 mg of product 1 are dissolved in 1.1 ml of distilled water; a solution of 140 µl of 1,6-Heptadiyne in 9.86 ml of DMSO are prepared separately, whereas 13.8 mg of benzydamine hydrochloride are dissolved in 0.5 ml of distilled water. The solution of hyaluronic acid is mixed with that of benzydamine and with 0.2 ml of that of 1,6-Heptadiyne; 0.1 ml of an aqueous solution obtained with 50 mg of $CuSO_4.5H_2O$ in 1 ml of $H_2O$ and 0.1 mL of an aqueous solution of 20 mg of ascorbic acid are then added. The mixture is stirred vortically for a few minutes. The rapidly formed gel incorporates the benzydamine hydrochloride inside.

Release Measurements of the Drug Benzydamine Hydrochloride from a Hydrogel Based on Hyaluronic Acid with 1,6-Heptadiyne Obtained with Catalytic $CuSO_4.5H_2O$ and Ascorbic Acid, Crosslinked According to the Structure Indicated Above The quantity of benzydamine hydrochloride released from the hydrogel, in 100 ml of distilled water, is determined by means of U.V. spectrophotometric measurements at $\lambda=308$ nm by interpolation of the absorbance values on a calibration line constructed using solutions of the drug at known concentration.

The maximum quantity of benzydamine hydrochloride is released over a period of about 6 h and is equal to 80% of the quantity of drug initially incorporated in the gel (see FIG. 30).

Formation of the Hydrogel of Hyaluronic Acid with 1,8-Nonadiyne Obtained with Catalytic $CuSO_4.5H_2O$ and Ascorbic Acid in an Aqueous/Organic Solvent in the Presence of Doxorubicin Hydrochloride 100 mg of product 1 are dissolved in 1.1 ml of distilled water; a solution of 200 µl of 1,8-Nonadiyne in 11.23 ml of DMSO are prepared separately, whereas 23.2 mg of doxorubicin hydrochloride are dissolved in 0.5 ml of distilled water. The solution of hyaluronic acid is mixed with that of doxorubicin and with 0.2 ml of that of 1,8-Nonadiyne; 0.1 ml of an aqueous solution obtained with 50 mg of $CuSO_4.5H_2O$ in 1 ml of $H_2O$ and 0.1 ml of an aqueous solution of 20 mg of ascorbic acid are then added. The mixture is stirred vortically for a few minutes. The rapidly formed gel (see FIG. 31) incorporates the doxorubicin hydrochloride inside.

Release Measurements of the Drug Doxorubicin Hydrochloride from a Hydrogel Based on Hyaluronic Acid with 1,8-Nonadiyne Obtained with Catalytic $CuSO_4.5H_2O$ The quantity of doxorubicin hydrochloride released from the hydrogel, in 100 ml of distilled water, is determined by means of U.V. spectrophotometric measurements at $\lambda=486$ nm by interpolation of the absorbance values on a calibration line constructed using solutions of the drug at known concentration.

The release measurements of the drug are performed on the hydrogel described above.

The maximum quantity of doxorubicin hydrochloride is released over a period of about 100 h and is equal to 14% of the quantity of drug initially incorporated in the gel (see FIG. 32).

The invention claimed is:

1. A process for the preparation of crosslinked derivatives of polycarboxylated polysaccharides, wherein at least one of the polysaccharide chains consists of a derivative of hyaluronic acid, crosslinked by means of "click chemistry"-type reactions, said process comprising the following phases:
   i) preparing partial ester, amide, thioester or anhydride derivatives of polycarboxylated polysaccharides comprising (a) a type (a) residue being a 1,3-unsaturated or a 1,3-dipole group, and (b) a type (b) residue being a dienophile or a dipolarophile group; and
   ii) reacting at least two products of step i), one comprising a polycarboxylated polysaccharide comprising a 1,3-unsaturated group and one comprising a polycarboxylated polysaccharided comprising a dienophile group, or one comprising a polycarboxylated polysaccharide comprising a 1,3-dipole group and one comprising a polycarboxylated polysaccharide comprising a dipolarophile group in a cycloaddition reaction to form covalent bonds between two chains of said polycarboxylated polysaccharides; wherein:
   said 1,3-unsaturated group is a member selected from the group consisting of 1,3-butadiene, 1-methoxy-3-trimethylsilyloxy-1,3-butadiene, cyclopentadiene, cyclohexadiene, and furan;
   said dienophile is selected from alkenes, alkynes or derivatives of alkenes or alkynes with one or more electron-attractor groups linked to the double or triple bond;
   said 1,3-dipole group is selected from derivatives of nitrile-oxides, azides, diazo-alkanes, allenes and nitrones; and
   said dipolarophile is selected from alkenes, alkynes or derivatives of alkenes or alkynes with one or more electron-attractor groups bound to the double or triple bond.

2. The process according to claim 1, wherein at least two of the partial derivatives obtained in phase i) have the following chemical structure a)

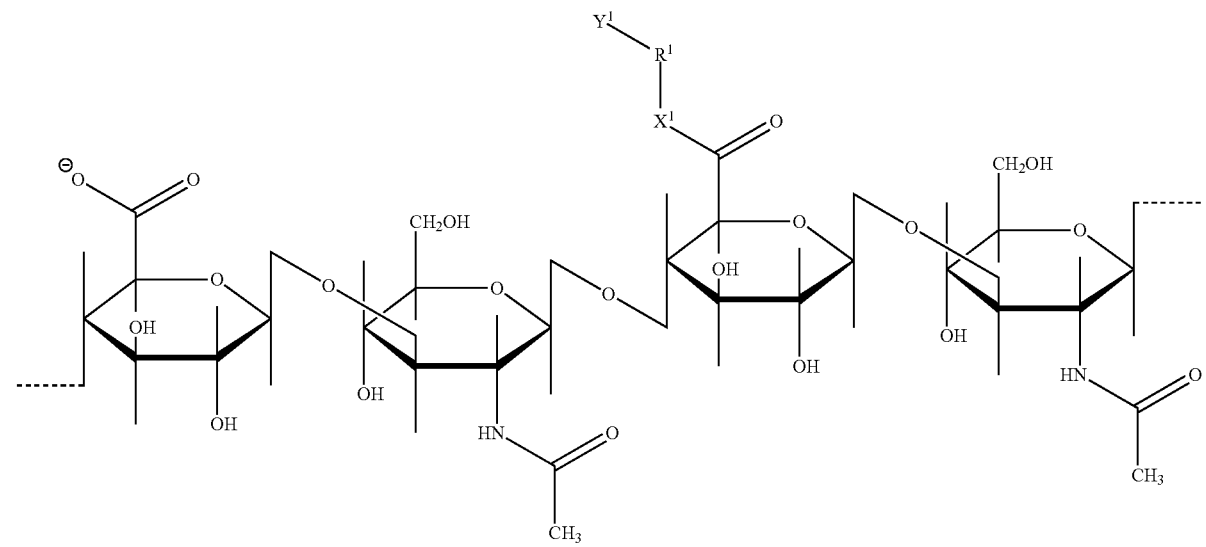

b)

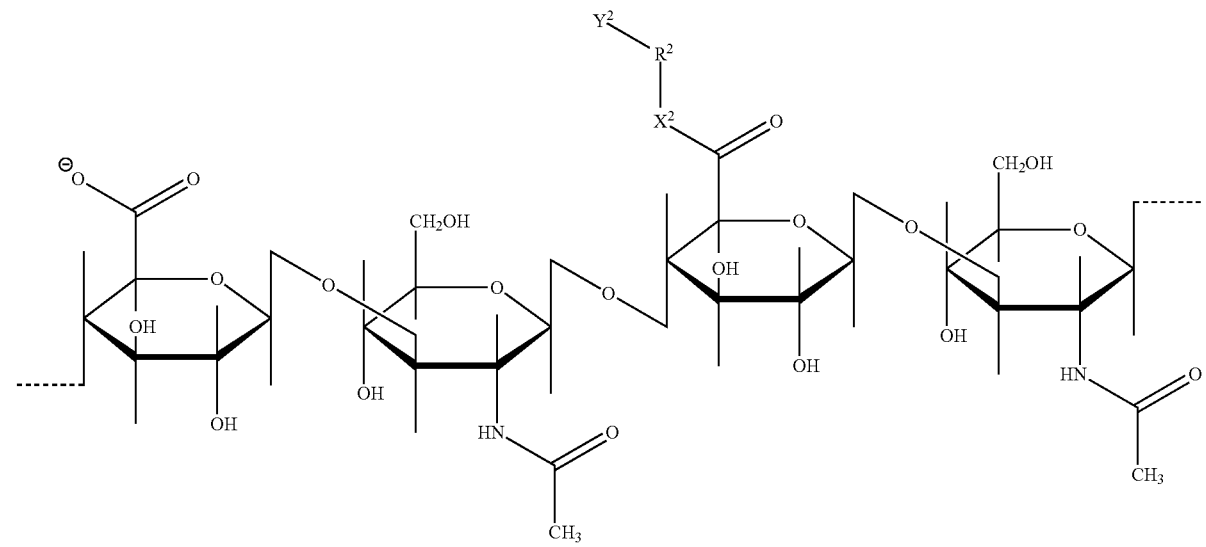

wherein the $X^i$, $R^i$ and $Y^i$ groups are thus defined:
$X^1$ and $X^2$ are independently O, NH, OC(O), S groups;
$R^1$ and $R^2$ are independently substituted or non-substituted aliphatic chains with a number of carbon atoms varying from 1 to 20, possibly containing heteroatoms, or groups of the aromatic, arylaliphatic, cyclo-aliphatic, heterocyclic series;
$Y^1$ and $Y^2$ are residues containing groups capable of reacting with each other in a Diels Alder cycloaddition reaction or a 1,3-dipolar cycloaddition, wherein:
said 1,3-unsaturated group is selected from derivatives of 1,3-dienes;
said dienophile is selected from alkenes, alkynes or derivatives of alkenes or alkynes with one or more electron-attractor groups linked to the double or triple bond;
said 1,3-dipole group is selected from derivatives of nitrile-oxides, azides, diazo-alkanes, allenes and nitrones; and
said dipolarophile is selected from alkenes, alkynes or derivatives of alkenes or alkynes with one or more electron-attractor groups bound to the double or triple bond, and preferably from acrylates, acrylamides, fumarates, vinylketones, nitro-alkenes, nitro-alkynes, maleic anhydride, methylacetylene and quinones.

3. The process according to claim 1, wherein phase ii) is carried out in an aqueous solvent or aprotic polar organic solvent or in a mixed solvent.

4. The process according to claim 1, wherein phase ii) is carried out with concentrations of the polysaccharide partial derivatives obtained in phase i) ranging from 1 to 500 mg/ml.

5. The process according to claim 1, characterized in that both of the phases i) and ii) are carried out at a reaction temperature ranging from 4 to 60° C.

6. The process according to claim 1, wherein phase ii) includes stirring during said cyclo addition reaction for a time ranging from a few seconds to 30 minutes.

7. The process according to claim 1, wherein phase ii) is carried out with catalysis in the presence of a Cu(I) salt, present in the aqueous reaction mixture at a final concentration ranging from 1 to 50 mg/ml, or with catalysis of a system which generates Cu(I) in situ.

8. A crosslinked derivative of a polycarboxylated polysaccharide, wherein at least one of the polysaccharide chains consists of a derivative of hyaluronic acid, crosslinked by means of a "click chemistry" reaction, prepared by the process comprising:

i) preparing partial ester, amide, thioester or anhydride derivatives of polycarboxylated polysaccharides comprising (a) a type (a) residue being a 1,3-unsaturated or a 1,3-dipole group, and (b) a type (b) residue being a dienophile or a dipolarophile group; and ii) reacting at least two products of step i), one comprising a polycarboxylated polysaccharide comprising a 1,3-unsaturated group and one comprising a polycarboxylated polysaccharided comprising a dienophile group, or one comprising a polycarboxylated polysaccharide comprising a 1,3-dipole group and one comprising a polycarboxylated polysaccharide comprising a dipolarophile group in a cycloaddition reaction to form covalent bonds between two chains of said polycarboxylated polysaccharides; wherein:

said 1,3-unsaturated group is member selected from the groan consisting of 1,3-butadiene, 1-methoxy-3-trimethylsilyloxy-1,3-butadiene, cyclopentadiene, cyclohexadiene, and furan;

said dienophile is at least one member selected from the group consisting of alkenes, alkynes and derivatives of alkenes or alkynes with one or more electron-attractor groups linked to the double or triple bond;

said 1,3-dipole group is at least one member selected from the group consisting of derivatives of nitrile-oxides, azides, diazo-alkanes, allenes and nitrones; and said dipolarophile is at least one member selected from the group consisting of alkenes, alkynes or derivatives of alkenes or alkynes with one or more electron-attractor groups bound to the double or triple bond.

9. The crosslinked derivative according to claim 8, wherein:
said dienophile is at least one member selected from the group consisting of acrylates, acrylamides, fumarates, vinylketones, nitro-alkenes, nitro-alkynes, maleic anhydride and quinones;
said 1,3-dipole group is an azide or a derivative of an azide; and
said dipolarophile is at least one member selected from the group consisting of acrylamides, fumarates, vinylketones, nitro-alkenes, nitro-alkynes, maleic anhydride, methylacetylene and quinones.

10. The crosslinked derivative according to claim 8, wherein at least two of said products of step i) have the following structure;

a)

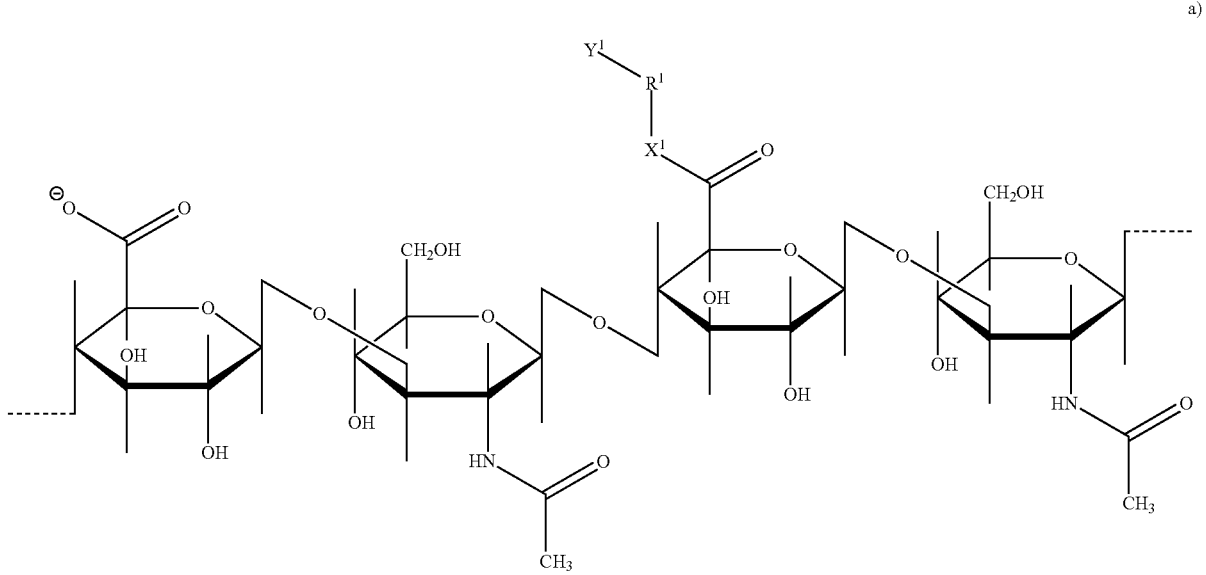

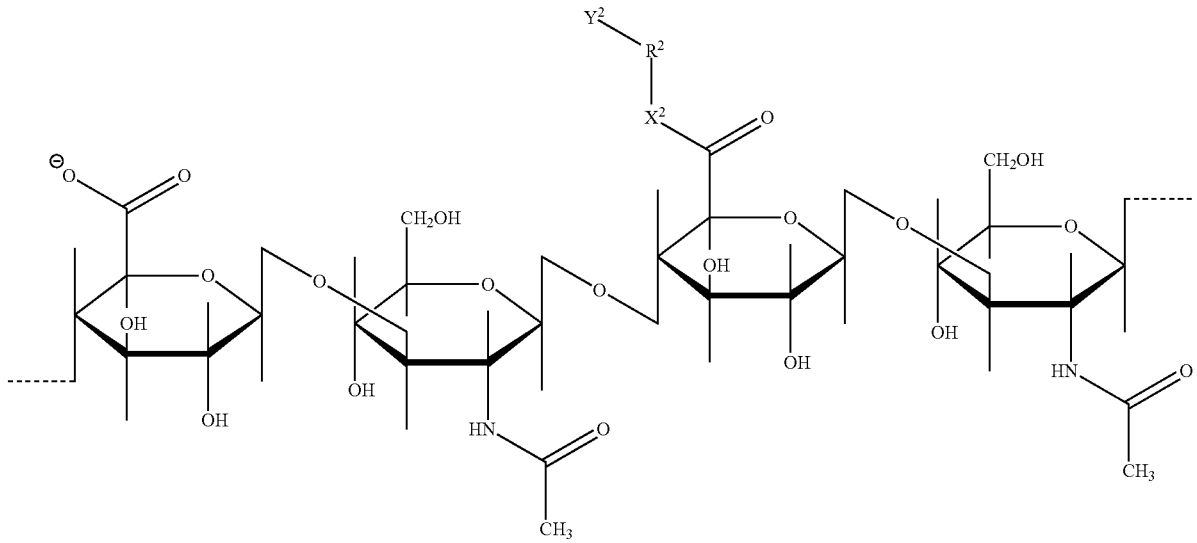

b)

wherein the $X^i$, $R^i$ and $Y^i$ groups are defined as follows:

$X^1$ and $X^2$ are independently O, NH, OC(O), S groups;

$R^1$ and $R^2$ are each independently a substituted or non-substituted aliphatic chain with a lumber of carbon atoms varying from 1 to 20, or groups of the aromatic, arylaliphatic, cyclo-aliphatic, heterocyclic series, $Y^1$ and $Y^2$ are a pair of (1,3-unsaturated, dienophile), or (1,3-dipole, dipolarophile) type, wherein:

the 1,3-unsaturated group is a member selected from the group consisting of 1,3-butadiene, 1-methoxy-3-trimethylsilyloxy-1,3-butadiene, cyclopentadiene, cyclohexadiene, and furan;

the dienophile is member selected from the group consisting of alkenes, alkynes or derivatives of alkenes or alkynes with one or more electron-attractor groups linked to the double or triple bond, the 1,3-dipole group is at least one member selected from the group consisting of derivatives of nitrile-oxides, azides, diazo-alkanes, allenes and nitrones, the dipolarophile is at least one member selected from the group consisting of alkenes, alkynes or derivatives of alkenes or alkynes with one or more electron-attractor groups bound to the double or triple bond.

11. The crosslinked derivative according to claim 8, wherein said products of step i) have the following chemical structure

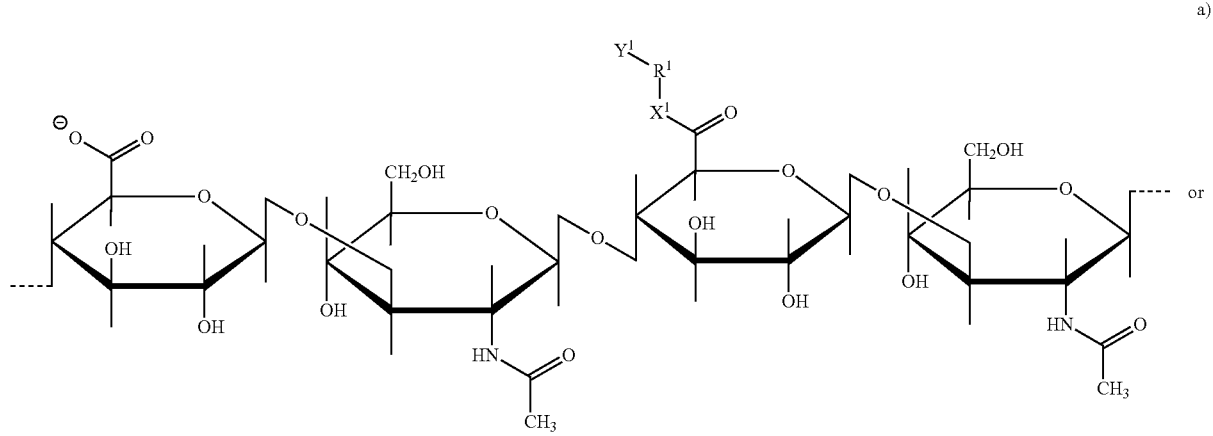

a)

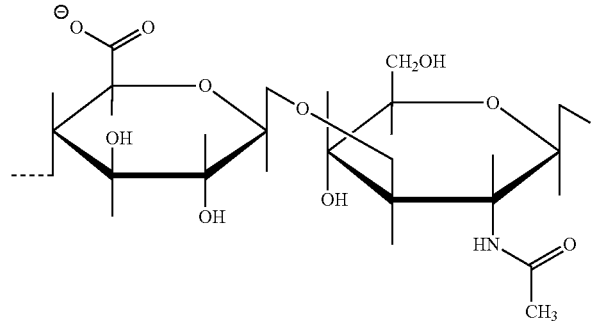
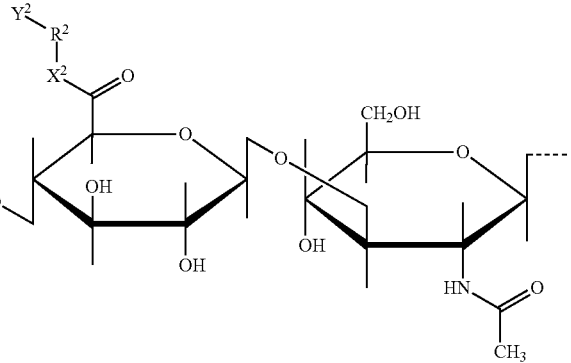

wherein the $X^i$, $R^i$ and $Y^i$ groups are defined:
$X^1$ and $X^2$ are independently an O, NH, OC(O), or S group;
$R^1$ and $R^2$ are independently a substituted or non-substituted aliphatic chain with a number of carbon atoms varying from 1 to 20;
$Y^1$ and $Y^2$ are a pair of (1,3-unsaturated, dienophile), or (1,3-dipole, dipolarophile) type, wherein:
the 1,3-unsaturated group is a member selected from the group consisting of 1,3-butadiene, 1-methoxy-3-trimethylsilyloxy-1,3-butadiene, cyclopentadiene, cyclohexadiene, and furan;
the dienophile is member selected from the group consisting of alkenes, alkynes or derivatives of alkenes or alkynes with one or more electron-attractor groups linked to the double or triple bond,
the 1,3-dipole group is at least one member selected from the group consisting of derivatives of nitrile-oxides, azides, diazo-alkanes, allenes and nitrones,
the dipolarophile is at least one member selected from the group consisting of alkenes, alkynes or derivatives of alkenes or alkynes with one or more electron-attractor groups bound to the double or triple bond.

12. The crosslinked derivative according to claim 8, wherein free carboxylic groups of said hyaluronic acid derivative are present in the form of free carboxylic acids or carboxylated salts with tetraalkylammonium or an alkaline or alkaline-earth metal.

13. The crosslinked derivative according to claim 12, wherein said crosslinked derivative comprises at least one polysaccharide chain that comprises a polycarboxylated polysaccharide selected from the group consisting of glycosaminoglycanes and a natural or synthetic polysaccharide and salts thereof.

14. The crosslinked derivative according to claim 12, wherein said derivative is in the form of hydrogels.

15. The crosslinked derivative according to claim 14, wherein said hydrogel is a viscous and mucoadhesive fluid, or a compact three-dimensional structure of the wall-wall type.

16. The crosslinked derivative according to claim 14, wherein said hydrogel comprises at least one member selected from the group consisting of biologically or pharmacologically active molecules, peptides, proteins, oligo- and poly-nucleotides, additional polymers and cellular material.

17. A method for providing osteoarticular viscosupplementation to a patient in need thereof which comprises administering to said patient a hydrogel according to claim 14.

18. A controlled release system of molecules and/or macromolecules having a biological or pharmacological activity, comprising, as matrix, a crosslinked derivative in the form of a hydrogel according to claim 14.

19. A controlled release system of oligo- and poly-nucleotides for use in gene therapy, comprising, as matrix, a crosslinked derivative in the form of a hydrogel according to claim 14.

20. A matrix in the form of a hydrogel, consisting of a crosslinked derivative according to claim 14, containing cellular material for use in tissue engineering or regeneration.

21. The system according to claim 18, wherein the molecules and/or macromolecules having a biological or pharmacological activity are selected from proteins, growth factors, enzymes, antitumoral drugs, cytostatics, steroid and non-steroid anti-inflammatory drugs, antibiotics, antimicrobial drugs, antiviral drugs, antifungal drugs, anesthetics, analgesics, narcotics, cholinergic and adrenergic agonists and antagonists, antithrombotic drugs, anticoagulants, haemostatic drugs, fibrinolytic and thrombolytic drugs for topic, subcutaneous, intramuscular and intra-articular use.

22. A method for the preparation of a controlled release system of drugs in the form of a gel according to claim 18, wherein one or more biologically or pharmacologically active molecules are dissolved in the reaction solvent together with the polysaccharide partial derivatives to be crosslinked.

23. The crosslinked derivative according to claim 12, wherein said alkaline or alkaline-earth metal is at least one member selected from the group consisting of sodium, potassium, magnesium and calcium.

24. The crosslinked derivative according to claim 13, wherein said glycosaminoglycane is at least one member selected from the group consisting of chondroitins, sulfated dermatans, sulfated heparans and heparins, said natural polysaccharide is alginic acid and said synthetic polysaccharide is carboxymethylcellulose (CMC) or hydroxyproplylenemethyl cellulose (HPMC).

* * * * *